United States Patent [19]
Albizati et al.

[11] Patent Number: 6,001,851
[45] Date of Patent: Dec. 14, 1999

[54] HIV PROTEASE INHIBITORS

[75] Inventors: Kim F. Albizati, San Diego; Siegfried H. Reichi; Michael D. Varney, both of Solana Beach; Kanyin E. Zhang, Cardiff by the Sea, all of Calif.; Takuo Kobayashi, Takatsuki, Japan

[73] Assignee: Agouron Pharmaceuticals, Inc., La Jolla, Calif.

[21] Appl. No.: 09/041,391

[22] Filed: Mar. 12, 1998

Related U.S. Application Data

[60] Provisional application No. 60/040,741, Mar. 13, 1997.

[51] Int. Cl.$^6$ .......................... C07D 217/20; A61K 31/47
[52] U.S. Cl. ............................................ 514/307; 546/146
[58] Field of Search .............................. 546/146; 514/307

[56] References Cited

U.S. PATENT DOCUMENTS

| | | | |
|---|---|---|---|
| 5,063,208 | 11/1991 | Rosenberg et al. | 514/19 |
| 5,142,056 | 8/1992 | Kempe et al. | 546/265 |
| 5,157,041 | 10/1992 | Handa et al. | 514/314 |
| 5,196,438 | 3/1993 | Martin et al. | 514/311 |
| 5,204,471 | 4/1993 | Negele et al. | 546/144 |
| 5,235,039 | 8/1993 | Heath, Jr. et al. | 530/328 |
| 5,434,265 | 7/1995 | Fritz et al. | 546/146 |
| 5,463,104 | 10/1995 | Vazquez et al. | 514/533 |
| 5,484,926 | 1/1996 | Dressman | 546/114 |
| 5,514,802 | 5/1996 | Fritz et al. | 546/146 |
| 5,527,829 | 6/1996 | Kalish | 514/604 |
| 5,705,647 | 1/1998 | Babu et al. | 546/146 |
| 5,714,518 | 2/1998 | Reich et al. | 514/616 |

FOREIGN PATENT DOCUMENTS

| | | |
|---|---|---|
| 2075666 | 2/1993 | Canada . |
| 0 337 714 A2 | 10/1989 | European Pat. Off. . |
| 0 346 847 A2 | 12/1989 | European Pat. Off. . |
| 0 356 223 A2 | 2/1990 | European Pat. Off. . |
| 0 361 341 A2 | 4/1990 | European Pat. Off. . |
| 0 402 646 A1 | 12/1990 | European Pat. Off. . |
| 0 432 694 A2 | 6/1991 | European Pat. Off. . |
| 0 432 695 A2 | 6/1991 | European Pat. Off. . |
| 0 434 365 A2 | 6/1991 | European Pat. Off. . |
| 0 490 667 A2 | 6/1992 | European Pat. Off. . |
| 0 498 680 A1 | 8/1992 | European Pat. Off. . |
| 0 526 009 A1 | 2/1993 | European Pat. Off. . |
| 0 533 000 A1 | 3/1993 | European Pat. Off. . |
| 0 539 192 A1 | 4/1993 | European Pat. Off. . |
| 0 560 268 A1 | 9/1993 | European Pat. Off. . |
| WO 91/08221 | 6/1991 | WIPO . |
| WO 93/04043 | 3/1993 | WIPO . |
| WO 93/13066 | 7/1993 | WIPO . |
| WO 93/23379 | 11/1993 | WIPO . |
| WO 94/04492 | 3/1994 | WIPO . |
| WO 94/05639 | 3/1994 | WIPO . |
| WO 95/09843 | 4/1995 | WIPO . |

OTHER PUBLICATIONS

Kong–Teck Chong et al., "Peptidomimetic HIV Protease Inhibitors: Phosphate Prodrugs with Improved Biological Activities," *J. Med. Chem.*, 36:2575–2577 (1993).

Arun K. Ghosh et al., "3–Tetrahydrofuran and Pyran Urethanes as High–Affinity $P_2$–Ligands for HIV–1 Protease Inhibitors," *J. Med. Chem.*, 36:292–294 (1993).

Arun K. Ghosh et al., "Cyclic Sulfolanes as Novel and High Affinity $P_2$ Ligands for HIV–1 Protease Inhibitors," *J. Med. Chem.*, 36:924–927 (1993).

Arun K. Ghosh et al., "Potent HIV Protease Inhibitors: The Development of Tetrahydrofuranylglycines as Novel $P_2$–Ligands and Pyrazine Amides as $P_3$–Ligands," *J. Med. Chem.*, 36:2300–2310 (1993).

Jenny C. Gilbert et al., "NMR Studies of Four Isomers of Decahydroisoquinoline–3(S)–carboxylic Acid and a Potent HIV Proteinase Inhibitor Incorporating the (S,S,S) Isomer," *J. Chem. Soc. Perkin Trans. 2,*, pp. 475–479 (1993).

Ioannis N. Houpis et al., "Towards the Synthesis of HIV–Protease Inhibitors. Synthesis of Optically Pure 3–Carboxyl–decahydroisoquinolines," *Tetrahedron Letters*, vol. 34, No. 16, pp. 2593–2596 (1993).

Joel R. Huff, "HIV Protease: A Novel Chemotherapeutic Target for AIDS," *J. Med. Chem.*, vol. 34, No. 8, pp. 2305–2314 (1991).

J.V.N. Vara Prasad et al., "$P_3$ and $P_3'$ substituted analogs of hydroxyethylamine inhibitors of HIV protease," *Peptides: Chemistry & Biology*, pp. 721–722 (1991).

Daniel H. Rich et al., "Effect of Hydroxyl Group Configurations in Hydroxyethylamine Dipeptide Isosteres on HIV Protease Inhibition. Evidence for Multiple Binding Modes," *J. Med. Chem.*, 34:1222–1225 (1991).

Noel A. Roberts et al., "Rational Design for Peptide–Based HIV Proteinase Inhibitors," *Science*, vol. 248, pp. 358–361 (1990).

Tim F. Tam et al., "Intriguing Structure—Activity Relations Underlie the Potent of HIV Protease by Norstatine–Based Peptides," *J. Med. Chem.*, 35:1318–1320 (1992).

Suvit Thaisrivongs et al., "Inhibitors of the Protease from Human Immunodeficiency Virus: Design and Modeling of a Compound Containing a Dihydroxyethylene Isostere Insert with High Binding Affinity and Effective Antiviral Activity," *J. Med. Chem.*, 34:2344–2356 (1991).

Wayne J. Thompson et al., "3'–Tetrahydrofuranylglycine as a Novel, Unnatural Amino Acid Surrogate for Asparagine in the Design for Inhibitors of the HIV Protease," *J. Am. Chem. Soc.*, 115:801–803 (1993).

T.A. Lyle, et al., "Benzocycloalkyl Amines as Novel C–Termini for HIV Protease Inhibitors," *J. Med. Chem.*, 34:1228–1230 (1991).

(List continued on next page.)

*Primary Examiner*—Zinna Northington Davis

[57] ABSTRACT

HIV protease inhibitors, obtainable by chemical synthesis, inhibit or block the biological activity of the HIV protease enzyme, causing the replication of the HIV virus to terminate. These compounds, as well as pharmaceutical compositions that contain these compounds and optionally other anti-viral agents as active ingredients, are suitable for treating patients or hosts infected with the HIV virus, which is known to cause AIDS.

34 Claims, No Drawings

OTHER PUBLICATIONS

Steven D. Young et al., "HIV–1 Protease Inhibitors Based on Hydroxyethylene Dipeptide Isosteres: An Investigation into the Role of the $P_1'$ Side Chain on Structure–Activity," *J. Med. Chem.*, 35:1702–1709 (1992).

Rich, *Chemical Abstracts,* vol. 114, No. 15 Abstract No. 114:143998 (1991).

Abstract for Japanese Patent Appln. No. 95–248183 to Inaba, et al., dated Apr. 1997.

Abstract for Japanese Patent Appln. No. 95–248184 to Deason, et al., dated Apr. 1997.

Ratner, et al., "Complete Nucleotide Sequence of the AIDS Virus, HTLV–III," *Nature,* vol. 313 (1985), pp. 277–284.

Rose, et al., "Regulation of Autoproteolysis of the HIV–1 and HIV–2 Proteases with Engineered Amino Acid Substitutions," *The Journal of Biological Chemistry,* vol. 268, No. 16 (1993), pp. 11939–11945.

Menge, et al., "Structure–Function Analysis of the Mammalian DNA Polymerase β Active Site: Role of Aspartic Acid 256, Arginine 254, and Arginine 258 in Nucleotidyl Transfer," *Biochemistry,* vol. 34, (1995), pp. 15934–15942.

Celis, "Chain–terminating Mutants Affecting a Periplasmic Binding Protein Involved in the Active Transport of Arginine and Ornithine in *Escherichia coli,*" *The Journal of Biological Chemistry,* vol. 256, No. 2 (1981), pp. 773–779.

Morrison, "Kinetics of the Reversible Inhibition of Enzyme–Catalysed Reactions by Tight–Binding Inhibitors," *Biochemica et Biophysica Acta,* vol. 185 (1969), pp. 269–286.

Alley, et al., "Feasibility of Drug Screening with Panels of Human Tumor Cell Lines Using a Microculture Tetrazolium Assay," *Cancer Research,* vol. 48 (1988), pp. 589–601.

Longer, et al., "Preformulation Studies of a Novel HIV Protease Inhibitor, AG1343," *Journal of Pharmaceutical Sciences,* vol. 84, No. 9, Sep. 1995, pp. 1090–1093.

HIV PROTEASE INHIBITORS

RELATED APPLICATION DATA

This application claims priority benefits under 35 U.S.C. §119 based on U.S. Provisional Patent Application No. 60/040,741, filed Mar. 13, 1997, which application is entirely incorporated herein by reference.

BACKGROUND AND SUMMARY OF THE INVENTION

This invention relates to a novel series of chemical compounds useful as HIV protease inhibitors and to the use of such compounds as antiviral agents.

Acquired Immune Deficiency Syndrome (AIDS) is a relatively newly recognized disease or condition. AIDS causes a gradual breakdown of the body's immune system as well as progressive deterioration of the central and peripheral nervous systems. Since its initial recognition in the early 1980's, AIDS has spread rapidly and has now reached epidemic proportions within a relatively limited segment of the population. Intensive research has led to the discovery of the responsible agent, human T-lymphotropic retrovirus III (HTLV-III), now more commonly referred to as the human immunodeficiency virus or HIV.

HIV is a member of the class of viruses known as retroviruses. The retroviral genome is composed of RNA which is converted to DNA by reverse transcription. This retroviral DNA is then stably integrated into a host cell's chromosome and, employing the replicative processes of the host cells, produces new retroviral particles and advances the infection to other cells. HIV appears to have a particular affinity for the human T-4 lymphocyte cell which plays a vital role in the body's immune system. HIV infection of these white blood cells depletes this white cell population. Eventually, the immune system is rendered inoperative and ineffective against various opportunistic diseases such as, among others, pneumocystic carini pneumonia, Kaposi's sarcoma, and cancer of the lymph system.

Although the exact mechanism of the formation and working of the HIV virus is not understood, identification of the virus has led to some progress in controlling the disease. For example, the drug azidothymidine (AZT) has been found effective for inhibiting the reverse transcription of the retroviral genome of the HIV virus, thus giving a measure of control, though not a cure, for patients afflicted with AIDS. The search continues for drugs that can cure or at least provide an improved measure of control of the deadly HIV virus.

Retroviral replication routinely features post-translational processing of polyproteins. This processing is accomplished by virally encoded HIV protease enzyme. This yields mature polypeptides that will subsequently aid in the formation and function of infectious virus. If this molecular processing is stifled, then the normal production of HIV is terminated. Therefore, inhibitors of HIV protease may function as anti-HIV viral agents.

HIV protease is one of the translated products from the HIV structural protein pol gene. This retroviral protease specifically cleaves other structural polypeptides at discrete sites to release these newly activated structural proteins and enzymes, thereby rendering the virion replication-competent. As such, inhibition of the HIV protease by potent compounds may prevent proviral integration of infected T-lymphocytes during the early phase of the HIV-1 life cycle, as well as inhibit viral proteolytic processing during its late stage. Additionally, the protease inhibitors may have the advantages of being more readily available, longer lived in virus, and less toxic than currently available drugs, possibly due to their specificity for the retroviral protease.

In accordance with this invention, there is provided a novel class of chemical compounds that can inhibit and/or block the activity of the HIV protease, which halts the proliferation of HIV virus, pharmaceutical compositions containing these compounds, and the use of the compounds as inhibitors of the HIV protease.

The present invention relates to compounds falling within formula (9) below, and pharmaceutically acceptable salts, prodrugs, and solvates thereof, that inhibit the protease encoded by human immunodeficiency virus (HIV) type 1 (HIV-1) or type 2 (HIV-2). These compounds are useful in the treatment of infection by HIV and the treatment of the acquired immune deficiency syndrome (AIDS). The compounds, their pharmaceutically acceptable salts, and the pharmaceutical compositions of the present invention can be used alone or in combination with other antivirals, immunomodulators, antibiotics or vaccines. Compounds of the present invention can also be used as prodrugs. Methods of treating AIDS, methods of treating HIV infection and methods of inhibiting HIV protease are disclosed.

The compounds of the present invention are of the formula (9):

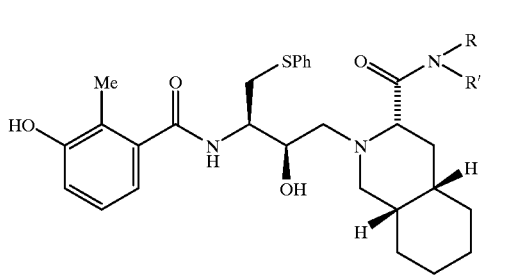

wherein:

R and R' are independently selected from H, a substituted or unsubstituted alkyl-$OR_1$ group, a cycloalkyl group substituted with a $(C_1-C_6)$alkyl group or a $(C_1-C_6)$alkyl-OH group, a heterocycle group substituted with a $(C_1-C_6)$alkyl group or a $(C_1-C_6)$alkyl-OH group, an alkyl-$NR_2R_3$ group, or an alkyl-$S(X)(Y)R_4$ group, wherein $R_1$ is H, a substituted or unsubstituted alkyl group, or an acyl group;

$R_2$ and $R_3$ are each independently selected from H, substituted or unsubstituted alkyl, cycloalkyl, heterocycle, and aryl groups, and acyl and sulfonyl groups;

$R_4$ is H, a substituted or unsubstituted alkyl, cycloalkyl, heterocycle, or aryl group; and X and Y are each independently selected from =O and nothing;

or a pharmaceutically acceptable prodrug, salt or solvate thereof.

Preferably in the compounds of formula 9, R is H. More preferably, R is H and R' is a cycloalkyl group selected from:

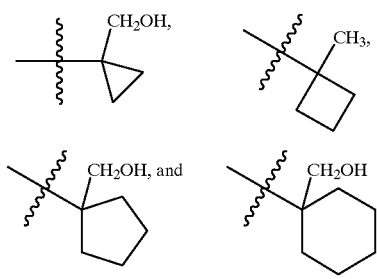

Preferably in the compounds of formula 9 when at least one of R and R' is an alkyl-OR$_1$ group, R$_1$ is H. Particularly when at least one of R and R' is an alkyl-OR$_1$ group, the alkyl-OR$_1$ is selected from —C(CH$_3$)$_2$CH$_2$OH, —CH(CH$_3$)CH$_2$OH, —CH$_2$CH$_2$OH, —C(CH$_3$)(CH$_2$OH)$_2$, —C(CH$_3$)$_2$—O—CH$_2$—O—CH$_3$, —C(CH$_3$)$_2$CH$_2$—O—CH$_2$—O—CH$_3$, and —C(CH$_3$)$_2$CH$_2$—O— acyl, or a pharmaceutically acceptable prodrug, salt or solvate thereof.

Preferably when at least one of R and R' is a cycloalkyl group substituted with a (C$_1$–C$_6$)alkyl group or a (C$_1$–C$_6$) alkyl—OH group, the cycloalkyl group is selected from:

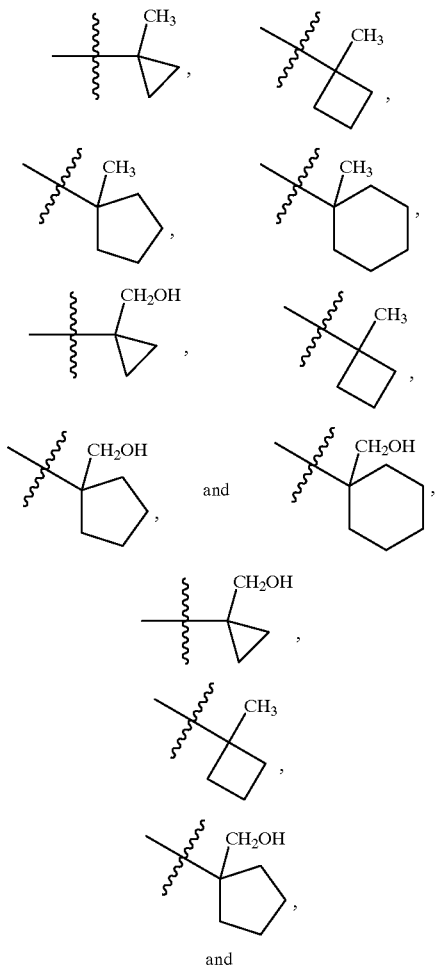

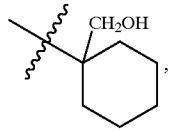

Preferably when at least one of R and R' is a heterocycle group substituted with a (C$_1$–C$_6$)alkyl group or a (C$_1$–C$_6$) alkyl—OH group, the heterocycle group is selected from:

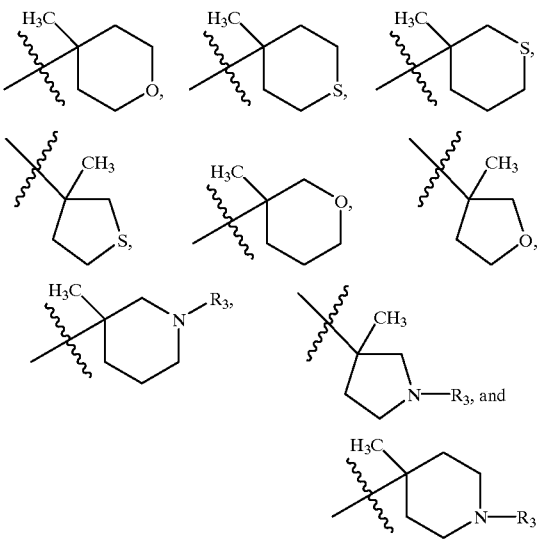

wherein R$_3$ is H, a substituted or unsubstituted alkyl, cycloalkyl, heterocycle, or aryl group, or an acyl or sulfonyl group.

A preferred species of the formula (9) is [3S-[2(2S*, 3S*),3 alpha,4a beta,8a beta]]-N-(1,1-dimethyl-2-hydroxyethyl)decahydro- 2-[2-hydroxy-3-[(3-hydroxy-2-methylbenzoyl)amino]-4-(phenylthio)butyl]-3-isoquinolinecarboxamide

21

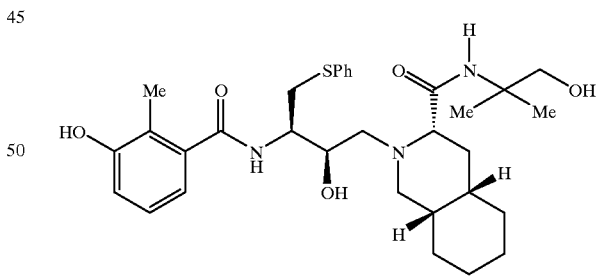

and its pharmaceutically acceptable salts, and its prodrug analogs. Preferred prodrugs can be obtained by replacing the hydrogen in one of the alcohol groups with an acyl group, and more preferably an amino acid acyl group.

The present invention further provides pharmaceutical formulations comprising an effective amount of a compound of formula (9) or a pharmaceutically acceptable salt thereof, in combination with a pharmaceutically acceptable carrier, such as a diluent or excipient.

The present invention further provides a method of treating AIDS comprising administering to a host or patient, such as a primate, an effective amount of a compound of the present invention.

The present invention further provides a method of inhibiting HIV replication comprising administering to an HIV infected cell, a cell susceptible to HIV infection or a host or patient, such as a primate, an effective amount of a compound of the present invention.

DETAILED DESCRIPTION OF THE INVENTION

The present invention provides new compounds falling within formula (9), as described above, that are useful for treating HIV infection and/or AIDS.

Applicants incorporate by reference U.S. Pat. No. 5,484,926, U.S. patent application Ser. Nos. 08/708,411 and 08/708,607, and Japanese Patent Application Nos. JP 95-248183 and JP 95-248184, with the caveat that the definitions of preferences, terms, variables, labels and the like used in each application are applicable only to the corresponding disclosure from that application.

In particular, since each of the above-identified applications incorporated by reference was prepared separately, the original applications may use in some instances the same term, label or variable to mean something different. For example, the variable "X" is used in each application, but each application has its own distinct definition of the substituent or moiety represented by this variable. It will be apparent to those skilled in the art that the terms, labels and variables in each application incorporated by reference are limited solely to the disclosure from that application, and may be replaced by other suitable terms, labels and variables or the like representing the particular substituents and moieties. Of course, those skilled in the art will realize that any suitable set of terms, labels and variables may be used to generically or more specifically represent the subject matter disclosed in the present application, including terms, labels, variables, and the like universally applicable to the incorporated disclosures of the above-identified applications and the following disclosure.

Compounds of the formula (9) may be prodrugs, which can serve to improve the pharmaceutical properties of the compounds, such as pharmacokinetic properties, for example, improved bioavailability or solubility. The preparation of prodrugs may be carried out by standard methods known to those skilled in the art. A preferred prodrug can be obtained by acylation or alkylation of the starting alcohol when R or R' is $CH(CH_3)_2CH_2OH$.

All temperatures stated herein are in degrees Celsius (°C.). All units of measurement employed herein are in weight units except for liquids which are in volume units.

The term "alkyl" as used herein refers to straight or branched chain groups, preferably, having one to eight, more preferably having one to six, and most preferably having from one to four carbon atoms. The term "$C_1$–$C_6$ alkyl", represents a straight or branched alkyl chain having from one to six carbon atoms. Exemplary $C_1$–$C_6$ alkyl groups include methyl, ethyl, n-propyl, isopropyl, butyl, isobutyl, sec-butyl, t-butyl, pentyl, neo-pentyl, hexyl, isohexyl, and the like. The term "$C_1$–$C_6$ alkyl" includes within its definition the term "$C_1$–$C_4$ alkyl".

The term "cycloalkyl" represents a saturated or partially saturated, mono- or poly-carbocylic ring, preferably having 5–14 ring carbon atoms. Exemplary cycloalkyls include monocyclic rings having from 3–7, preferably 3–6, carbon atoms, such as cyclopropyl, cyclobutyl, cyclopentyl, cyclohexyl, cycloheptyl and the like. An exemplary cycloalkyl is a $C_5$–$C_7$ cycloalkyl, which is a saturated hydrocarbon ring structure containing from five to seven carbon atoms.

The term "alkoxyl" represents —O—alkyl. An example of an alkoxyl is a $C_1$–$C_6$ alkoxyl, which represents a straight or branched alkyl chain having from one to six carbon atoms attached to an oxygen atom. Exemplary $C_1$–$C_6$ alkoxyl groups include methoxyl, ethoxyl, propoxyl, isopropoxyl, butoxyl, sec-butoxyl, t-butoxyl, pentoxyl, hexoxyl, and the like. $C_1$–$C_6$ alkoxyl includes within its definition a $C_1$–$C_4$ alkoxyl.

The term "aryl" as used herein refers to a carbocyclic or heterocyclic, aromatic, 5–14 membered monocyclic or polycyclic ring. Exemplary aryls include phenyl, naphthyl, anthryl, phenanthryl, thienyl, pyrrolyl, imidazolyl, pyrazolyl, furyl, isothiazolyl, furazanyl, isoxazolyl, thiazolyl, pyridyl, pyrazinyl, pyrimidinyl, pyridazinyl, triazinyl, benzo[b]thienyl, naphtho[2,3-b]thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxyalinyl, quinzolinyl, benzothiazolyl, benzimidazolyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl.

The term "aryloxyl", represents —O—aryl.

The term "hydrolyzable group" is a group, which when bonded to an oxygen, forms an ester, which can be hydrolyzed in vivo to a hydroxyl group. Exemplary hydrolyzable groups, which are optionally substituted, include acyl function, sulfonate function and phosphate function. For example, such hydrolyzable groups include blocked or unblocked amino acid residue, a hemisuccinate residue, and a nicotinate residue.

The term "halogen" represents chlorine, fluorine, bromine or iodine. The term "halo" represents chloro, fluoro, bromo or iodo.

The term "carbocycle" represents an aromatic or a saturated or a partially saturated 5–14 membered monocyclic or polycyclic ring, such as a 5- to 7-membered monocyclic or 7- to 10-membered bicyclic ring, wherein all the ring members are carbon atoms.

The term "heterocycle" represents an aromatic or a saturated or a partially saturated, 5–14 membered, monocylic or polycyclic ring, such as a 5- to 7-membered monocyclic or 7- to 10-membered bicyclic ring, having from one to three heteroatoms selected from nitrogen, oxygen and sulfur, and wherein any nitrogen and sulfur heteroatoms may optionally be oxidized, and any nitrogen heteroatom may optionally be quaternized. The heterocyclic ring may be attached at any suitable heteroatom or carbon atom. Examples of such heterocycles include decahydroisoquinolinyl, octahydrothieno[3,2-c]pyridinyl, piperidinyl, piperazinyl, azepinyl, pyrrolyl, pyrrolidinyl, pyrazolyl, pyrazolidinyl, imidazolyl, isobenzofuranyl, furazanyl, imidazolinyl, imidazolidinyl, pyridyl, pyrazinyl, pyrimidinyl, pyridazinyl, oxazolyl, oxazolidinyl, isoxazolyl, thianthrenyl, triazinyl, isoxazolidinyl, morpholinyl, thiazolyl, thiazolidinyl, isothiazolyl, quinuclidinyl, isothiazolidinyl, indolyl, quinolinyl, chromenyl, xanthenyl, isoquinolinyl, benzimidazolyl, thiadiazolyl, benzopyranyl, benzothiazolyl, benzoazolyl, furyl, tetrahydrofuryl, tetrahydropyranyl, thienyl, benzothienyl, benzo[b]thienyl, naphtho[2,3-b] thienyl, thiamorpholinyl, thiamorpholinylsulfoxide, thiamorpholinylsulfone, oxadiazolyl, triazolyl, tetrahydroquinolinyl, tetrahydrisoquinolinyl, phenoxathienyl, indolizinyl, isoindolyl, indazolyl, purinyl, isoquinolyl, quinolyl, phthalazinyl, naphthyridinyl, quinoxyalinyl, quinzolinyl, tetrahydroquinolinyl, cinnolinyl, pteridinyl, carbazolyl, beta-carbolinyl, phenanthridinyl, acridinyl, perimidinyl, phenanthrolinyl, phenazinyl, isothiazolyl, phenothiazinyl, and phenoxazinyl.

The term "thioether" includes S-aryl, such as phenylthio and naphthylthio; S-heterocycle where the heterocycle is saturated or partially saturated; S- ($C_5$–$C_7$) -cycloalkyl; and S-alkyl, such as $C_1$–$C_6$ alkylthio. In the thioether, the -aryl, the -heterocycle, the -cycloalkyl and the -alkyl can optionally be substituted. An example of a thioether is "$C_1$–$C_6$ alkylthio", which represents a straight or branched alkyl chain having from one to six carbon atoms attached to a sulfur atom. Exemplary $C_1$–C6 alkylthio groups include methylthio, ethylthio, propylthio, isopropylthio, butylthio, sec-butylthio, t-butylthio, pentylthio, hexylthio, and the like.

The term "mercapto" represents —SH.

The term "amino" represents —$NL_1L_2$, wherein $L_1$ and $L_2$ are preferably independently selected from oxygen, carbocycle, heterocycle, alkyl, sulfonyl and hydrogen; or $NC(O)L_3$, wherein $L_3$ is preferably alkyl, alkoxyl, hydrogen or —$NL_1L_2$. The aryl, alkyl and alkoxyl groups can optionally be substituted. An example of an amino is $C_1$–$C_4$ alkylamino, which represents a straight or branched alkyl chain having from one to four carbon atoms attached to an amino group. Exemplary $C_1$–$C_4$ alkylamino groups include methylamino, ethylamino, propylamino, isopropylamino, butylamino, sec-butylamino, and the like. Another example of an amino is di($C_1$–$C_4$)alkylamino, which represents two straight or branched alkyl chains, each having from one to four carbon atoms attached to a common amino group. Exemplary di($C_1$–$C_4$)alkylamino groups include dimethylamino, ethylmethylamino, methylpropylamino, ethylisopropylamino, butylmethylamino, sec-butylethylamino, and the like. An example of an amino is $C_1$–$C_4$ alkylsulfonylamino, which has a straight or branched alkyl chain having from one to four carbon atoms attached to a sulfonylamino moiety. Exemplary $C_1$–$C_4$ alkylsulfonylamino groups include methylsulfonylamino, ethylsulfonylamino, propylsulfonylamino, isopropylsulfonylamino, butylsulfonylamino, sec-butylsulfonylamino, t-butylsulfonylamino, and the like.

The term "acyl" represents $L_6C(O)L_4$, wherein $L_6$ is a single bond, —O or —N, and further wherein $L_4$ is preferably alkyl, amino, hydroxyl, alkoxyl or hydrogen. The alkyl and alkoxyl groups can optionally be substituted. An exemplary acyl is a $C_1$–$C_4$ alkoxycarbonyl, which is a straight or branched alkoxyl chain having from one to four carbon atoms attached to a carbonyl moiety. Exemplary $C_1$–$C_4$ alkoxycarbonyl groups include methoxycarbonyl, ethoxycarbonyl, propoxycarbonyl, isopropoxycarbonyl, butoxycarbonyl, and the like. Another exemplary acyl is a carboxy wherein L6 is a single bond and $L_4$ is alkoxyl, hydrogen, or hydroxyl. A further exemplary acyl is N-($C_1$–$C_4$)alkylcarbamoyl ($L_6$ is a single bond and $L_4$ is an amino), which is a straight or branched alkyl chain having from one to four carbon atoms attached to the nitrogen atom of a carbamoyl moiety. Exemplary N-($C_1$–$C_4$) alkylcarbamoyl groups include N-methylcarbamoyl, N-ethylcarbamoyl, N-propylcarbamoyl, N-isopropylcarbamoyl, N-butylcarbamoyl, and N-t-butylcarbamoyl, and the like. Yet another exemplary acyl is N,N-di($C_1$–$C_4$)alkylcarbamoyl, which has two straight or branched alkyl chains, each having from one to four carbon atoms attached to the nitrogen atom of a carbamoyl moiety.

Exemplary N,N-di($C_1$–$C_4$)alkylcarbamoyl groups include N,N-dimethylcarbamoyl, N,N-ethylmethylcarbamoyl, N,N-methylpropylcarbamoyl, N,N-ethylisopropylcarbamoyl, N,N-butylmethylcarbamoyl, N,N-sec-butylethylcarbamoyl, and the like.

The term "sulfinyl" represents —SO—$L_5$, wherein $L_5$ is preferably alkyl, amino, aryl, cycloalkyl or heterocycle. The alkyl, aryl, cycloalkyl and heterocycle can all optionally be substituted.

The term "sulfonyl" represents —$SO_2$—$L_5$, wherein $L_5$ is preferably alkyl, aryl, cycloalkyl, heterocycle or amino. The alkyl, aryl, cycloalkyl and heterocycle can all optionally be substituted. An example of a sulfonyl is a $C_1$–$C_4$ alkylsulfonyl, which is a straight or branched alkyl chain having from one to four carbon atoms attached to a sulfonyl moiety. Exemplary $C_1$–$C_4$ alkylsulfonyl groups include methylsulfonyl, ethylsulfonyl, propylsulfonyl, isopropylsulfonyl, butylsulfonyl, sec-butylsulfonyl, t-butylsulfonyl and the like.

As indicated above, many of the groups are optionally substituted. In fact, unless specifically noted, all of the groups defined by the terms defined in this application may be substituted or unsubstituted. For instance, when the term "alkyl" is used, it should be understood to encompass both substituted and unsubstituted alkyl unless specific exclusion of one or the other is positively stated. Examples of substituents for alkyl and aryl include mercapto, thioether, nitro ($NO_2$), amino, aryloxyl, halogen, hydroxyl, alkoxyl, and acyl, as well as aryl, cycloalkyl and saturated and partially saturated heterocycles. Examples of substituents for heterocycle and cycloalkyl include those listed above for alkyl and aryl, as well as aryl and alkyl.

Exemplary substituted aryls include a phenyl or naphthyl ring substituted with one or more substituents, preferably one to three substituents, independently selected from halo, hydroxy, morpholino ($C_1$–$C_4$) alkoxy carbonyl, pyridyl ($C_1$–$C_4$) alkoxycarbonyl, halo ($C_1$–$C_4$) alkyl, $C_1$–$C_4$ alkyl, $C_1$–$C_4$ alkoxy, carboxy, $C_1$–$C_4$ alkoxycarbonyl, carbamoyl, N-($C_1$–$C_4$) alkylcarbamoyl, amino, $C_1$–$C_4$ alkylamino, di($C_1$–$C_4$)alkylamino or a group of the formula —$(CH_2)_a$-$R^7$ where a is 1, 2, 3 or 4; and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino.

Another substituted alkyl is halo($C_1$–$C_4$)alkyl, which represents a straight or branched alkyl chain having from one to four carbon atoms with 1–3 halogen atoms attached to it. Exemplary halo($C_1$–$C_4$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like.

Another substituted alkyl is hydroxy($C_1$–$C_4$)alkyl, which represents a straight or branched alkyl chain having from one to four carbon atoms with a hydroxy group attached to it. Exemplary hydroxy($C_1$–$C_4$)alkyl groups include hydroxymethyl, 2-hydroxyethyl, 3-hydroxypropyl, 2-hydroxyisopropyl, 4-hydroxybutyl and the like.

Yet another substituted alkyl is $C_1$–$C_4$ alkylthio($C_1$–$C_4$) alkyl, which is a straight or branched $C_1$–$C_4$ alkyl group with a $C_1$–$C_4$ alkylthio group attached to it. Exemplary $C_1$–$C_4$ alkylthio($C_1$–$C_4$)alkyl groups include methylthiomethyl, ethylthiomethyl, propylthiopropyl, sec-butylthiomethyl, and the like.

Yet another exemplary substituted alkyl is heterocycle ($C_1$–$C_4$)alkyl, which is a straight or branched alkyl chain having from one to four carbon atoms with a heterocycle attached to it. Exemplary heterocycle($C_1$–$C_4$)alkyls include pyrrolylmethyl, quino-linylmethyl, 1-indolylethyl, 2-furylethyl, 3-thien-2-ylpropyl, 1-imidazolylisopropyl, 4-thiazolylbutyl and the like.

Yet another substituted alkyl is aryl($C_1$–$C_4$)alkyl, which is a straight or branched alkyl chain having from one to four carbon atoms with an aryl group attached to it. Exemplary aryl($C_1$–$C_4$)alkyl groups include phenylmethyl, 2-phenylethyl, 3-naphthyl-propyl, 1-naphthylisopropyl, 4-phenylbutyl and the like.

The heterocycle can, for example, be substituted with 1, 2 or 3 substituents independently selected from halo, halo ($C_1$–$C_4$) alkyl, $C_1$–$C_4$ alkyl, $C_1$–$C_4$ alkoxy, carboxy, $C_1$–$C_4$ alkoxycarbonyl, carbamoyl, N-($C_1$–$C_4$) alkylcarbamoyl, amino, $C_1$–$C_4$alkylamino, di($C_1$–$C_4$)alkylamino or a group having the structure —$(CH_2)_a$-$R^7$ where a is 1, 2, 3 or 4 and $R^7$ is hydroxy, $C_1$–$C_4$ alkoxy, carboxy, $C_1$–$C_4$ alkoxycarbonyl, amino, carbamoyl, $C_1$–$C_4$ alkylamino or di ($C_1$–$C_4$) alkylamino.

Examples of substituted heterocycles include 3-N-t-butyl carboxamide decahydroisoquinolinyl, 6-N-t-butyl carboxamide octahydro-thieno[3,2-c]pyridinyl, 3-methylimidazolyl, 3-methoxypyridyl, 4-chloroquinolinyl, 4-aminothiazolyl, 8-methylquinolinyl, 6-chloroquinoxalinyl, 3-ethylpyridyl, 6-methoxybenzimidazolyl, 4-hydroxyfuryl, 4-methylisoquinolinyl, 6,8-dibromoquinolinyl, 2-methyl-1,2,3,4-tetrahydroisoquinolinyl, N-methyl-quinolin-2-yl, 2-t-butoxycarbonyl-1,2,3,4-isoquinolin-7-yl and the like.

Exemplary heterocyclic ring systems represented by A or B include (1) 5-membered monocyclic ring groups such as thienyl, pyrrolyl, imidazolyl, pyrazolyl, furyl, isothiazolyl, furazanyl, isoxazolyl, thiazolyl and the like; (2) 6-membered monocyclic groups such as pyridyl, pyrazinyl, pyrimidinyl, pyridazinly, triazinyl and the like; and (3) polycyclic heterocyclic rings groups, such as decahydroisoquinolinyl, octahydro-thieno [3,2-c] pyridinyl, benzo[b]thienyl, naphtho[2,3-b]thianthrenyl, isobenzofuranyl, chromenyl, xanthenyl, and fully or partially saturated analogs thereof.

A cycloalkyl may be optionally substituted with 1, 2 or 3 substituents independently selected from halo, halo($C_1$–$C_4$) alkyl, $C_1$–$C_4$ alkyl, $C_1$–$C_4$ alkoxy, carboxy, $C_1$–$C_4$ alkoxycarbonyl, carbamoyl, N-($C_1$–$C_4$)alkylcarbamoyl, amino, $C_1$–$C_4$ alkylamino, di($C_1$–$C_4$)alkylamino or a group having the structure —$(CH_2)_a$-$R^7$ where a is 1, 2, 3 or 4 and $R^7$ is hydroxy, $C_1$–$C_4$ alkoxy, carboxy, $C_1$–$C_4$ alkoxycarbonyl, amino, carbamoyl, $C_1$–$C_4$ alkylamino or di($C_1$–$C_4$)alkylamino. Exemplary substituted cycloalkyl groups include 3-methylcyclopentyl, 4-ethoxycyclohexyl, 5-carboxycyclo-heptyl, 6-chlorocyclohexyl and the like.

Exemplary substituted hydrolyzable groups include N-benzyl glycyl, N-Cbz-L-valyl, and N-methyl nicotinate.

The compounds of the present invention have at least five asymmetric centers denoted by an asterisk in the formula (9) below:

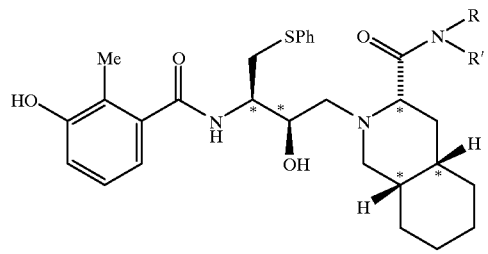

As a consequence of these asymmetric centers, the compounds of the present invention can occur in any of the possible stereoisomeric forms, and can be used in mixtures of stereoisomers, which can be optically active or racemic, or can be used alone as essentially pure stereisomers, i.e., at least 95% pure. All asymmetric forms, individual stereoisomers and combinations thereof, are within the scope of the present invention.

The individual stereoisomers may be prepared from their respective precursors by the procedures described above, by resolving the racemic mixtures, or by separating the diastereomers. The resolution can be carried out in the presence of a resolving agent, by chromatography or by repeated crystallization or by some combination of these techniques which are known in the art. Further details regarding resolutions can be found in Jacques et al., Enantiomers, Racemates, and Resolutions, John Wiley & Sons 1981.

Preferably, the compounds of the present invention are substantially pure, i.e, over 50% pure. More preferably, the compounds are at least 75% pure. Even more preferably, the compounds are more than 90% pure. Even more preferably, the compounds are at least 95% pure, more preferably, at least 97% pure, and most preferably at least 99% pure.

As mentioned above, the invention includes the pharmaceutically acceptable salts of the compounds defined by formula (9). A compound of this invention may possess a sufficiently acidic, a sufficiently basic, or both functional groups, and accordingly react with any of a number of inorganic or organic bases, and inorganic and organic acids, to form a pharmaceutically acceptable salt.

The term "pharmaceutically acceptable salt", as used herein, refers to salts of the compounds of the above formula which are substantially non-toxic to living organisms. Exemplary pharmaceutically acceptable salts include those salts prepared by reaction of the compounds of the present invention with a mineral or organic acid or an inorganic base. The reactants are generally combined in a mutual solvent such as diethylether or benzene, for acid addition salts, or water or alcohols for base addition salts. The salts normally precipitate out of solution within about one hour to about ten days and can be isolated by filtration or other conventional methods. Such salts are known as acid addition and base addition salts.

Acids that may be employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, oxalic acid, p-bromophenylsulfonic acid, carbonic acid, succinic acid, citric acid, benzoic acid, acetic acid, and the like.

Examples of pharmaceutically acceptable salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, g-hydroxybutyrate, glycollate, tartrate, methane-sulfonate, propanesulfonate, naphthalene-1-sulfonate, napththalene-2-sulfonate, mandelate and the like.

Preferred pharmaceutically acceptable acid addition salts are those formed with mineral acids such as hydrochloric acid and hydrobromic acid, and those formed with organic acids such as maleic acid and methanesulfonic acid.

Base addition salts include those derived from inorganic and organic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate and the like. The potassium and sodium salt forms are particularly preferred.

A "pharmaceutically acceptable prodrug" is intended to mean a compound that may be converted under physiological conditions or by solvolysis to a compound of the formula 9.

A "pharmaceutically acceptable solvate" is intended to mean a solvate that retains the biological effectiveness and properties of the biologically active components of compounds of formula 9.

Examples of pharmaceutically acceptable solvates include, but are not limited to, compounds of formula 9 in combination with water, isopropanol, ethanol, methanol, DMSO, ethyl acetate, acetic acid, or ethanolamine.

It should be recognized that the particular counterion forming a part of any salt of this invention is not of a critical nature, so long as the salt as a whole is pharmacologically acceptable and as long as the counterion does not contribute undesired qualities to the salt as a whole.

A preferred compound is compound 21

21

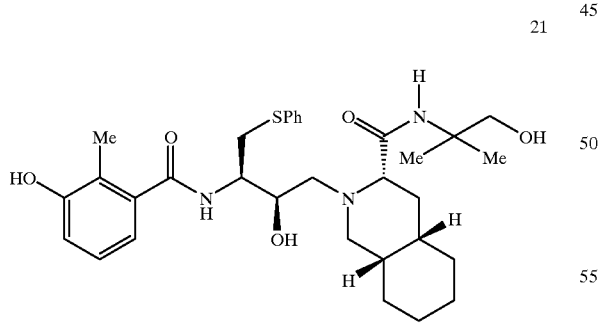

[3S-[2(2S*,3S*),3 alpha,4a beta,8a beta]]-N-(1,1-dimethyl-2-hydroxyethyl)decahydro-2-[2-hydroxy-3-[(3-hydroxy-2-methylbenzoyl)amino]-4-(phenylthio)butyl]-3-isoquinolinecarboxamide.

A process for making compound 21 is provided below. Compound 21 has also been obtained as a metabolite from the plasma of patients administered [3S-(3R,4aR*,8aR*, 2'S*,3'S*)] -2-[2'-hydroxy-3'-phenylthiomethyl-4'-aza-5'-oxo-5'-(2"-methyl-3"-hydroxyphenyl)pentyl] decahydroisoquinoline-3-N-t-butylcarboxamide methanesulfonic acid salt, which is disclosed in U.S. Pat. No. 5,484,926.

The compounds of formula 9 can be prepared according to the following Reaction Scheme I.

REACTION SCHEME I

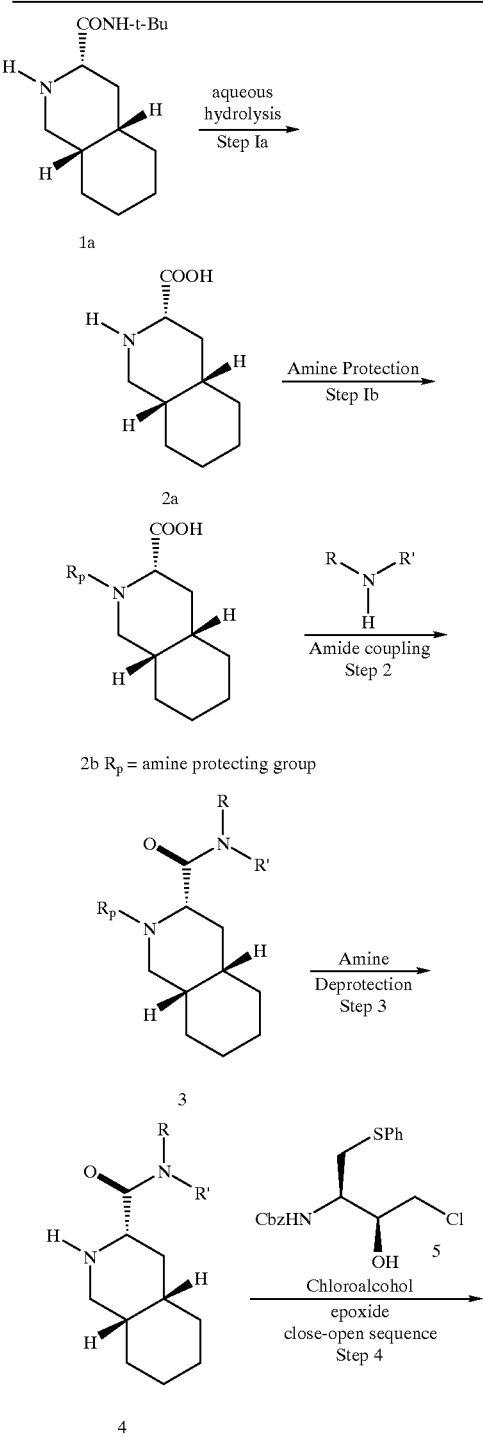

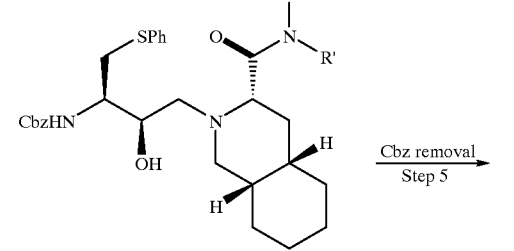

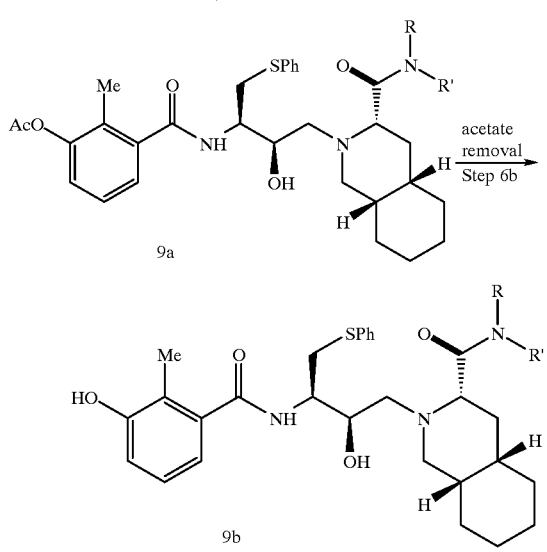

Compound 1a, perhydroisoquinoline, which is commercially available from NSC Technologies (Chicago, Ill.) or Procos SpA (Milan, Italy) is subjected to prolonged acid hydrolysis in step 1a to obtain compound 2a. A variety of inorganic acids may be used in either an aqueous/organic solvent mixture or in water alone at temperatures above 50° C. An example of such an inorganic acid is 6N aqueous HCl.

Substitutes for compound 1a include the corresponding esters 1b, thioesters 1c or other amides 1d:

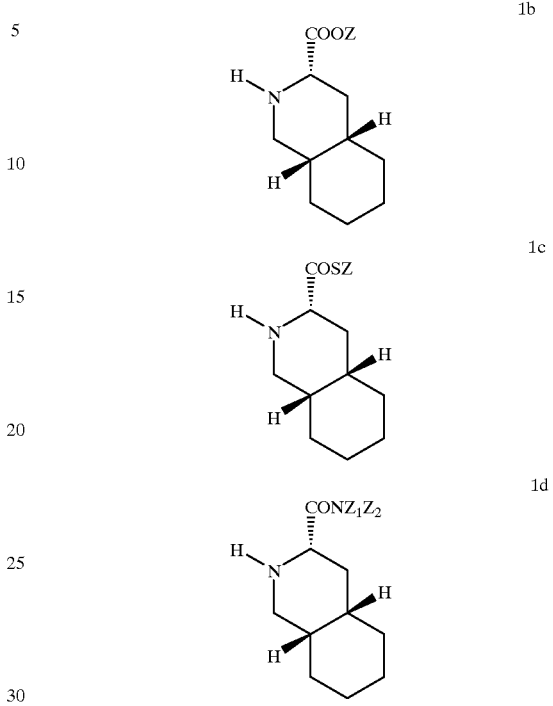

where Z, $Z_1$ and $Z_2$ may each independently be alkyl, cycloalkyl, heterocycle, or aryl.

Compound 2a is then protected at the amine nitrogen to obtain compound 2b in step 1b. The protecting group $R_p$ is defined as a suitably conjugating group to avoid unwanted decomposition of activated carboxylate derivatives of compound 2b in Step 2. Such protecting groups typically can be carbamate in origin, having a general structure of formula 11:

11

The identity of R" in formula 11 can be any alkyl, cycloalkyl, aryl, or heterocycle which can be removed easily in a deprotection step after Step 2. Examples of R" include, but are not limited to methyl, ethyl, propyl, isopropyl, n-butyl, isobutyl, t-butyl or higher branched or unbranched alkyl, 2,2,2-trichloroethyl, 2-trimethylsilylethyl, allyl, phenyl, substituted phenyl, benzyl, substituted benzyl, 9-fluorenylmethyl, 9-anthrylmethyl and higher polycyclic aromatic ring system. The following materials, as defined below, can be obtained from the Aldrich Chemical Co. (Sigma Aldrich Fluka):

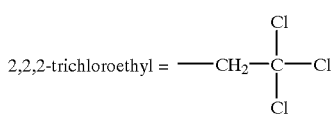

-continued 2-trimethylsilylethyl = 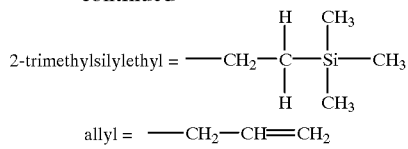

allyl = —CH$_2$—CH=CH$_2$ benzyl = —CH$_2$—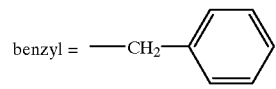

9-flourenylmethyl = 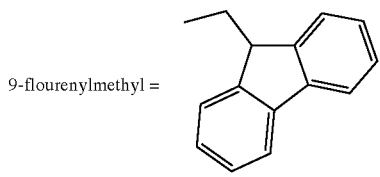

9-anthrylmethyl = 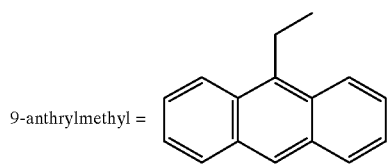

Such protecting groups typically can be installed by an acylation reaction of the corresponding haloformate ester 12a or a dicarbonate 12b:

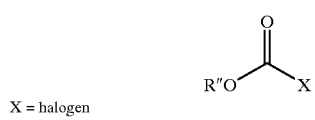

X = halogen

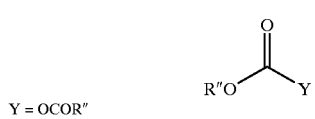

Y = OCOR″ in the presence of a suitable base in typical organic solvents for these types of reactions such as halogenated solvents, ethers and hydrocarbons. Such bases are typically inorganic, such as metal hydroxides, bicarbonates and carbonates or organic bases such as amines like triethylamine, diethylamine, diethyl isopropylamine, 1,8-diazabicyclo[2.2.2]octane (DABCO) or related di- or trialkylamines, as well as amidine bases like 1,8-diazabicyclo[5.4.0]undec-7-ene (DBU) and 1,8-diazabicyclo[4.3.0]non-5-ene (DBN). The following materials, as defined below, can be obtained from the Aldrich Chemical Co. (Sigma Aldrich Fluka):

DABCO = 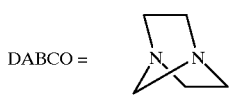

DBU = 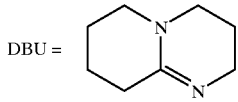

DBN = 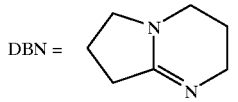

These reactions are typically run anywhere from below room temperature to approximately 100° C.

The amide coupling Step 2 can be accomplished in any number of fashions depending on how the carboxyl group is activated. A group J is installed in Step 2 by reaction of the carboxylic acid 2b to produce the activated derivative 2c.

Step 2

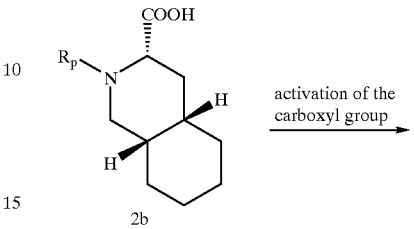

2b $R_p$ = amine protecting group

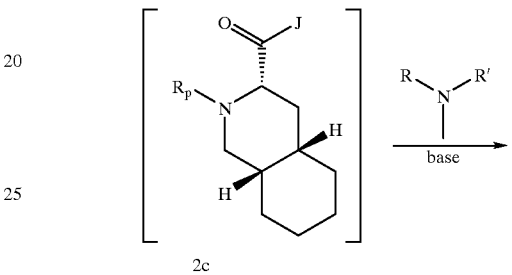

2c

J = leaving group

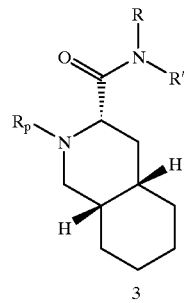

3

The group J can be any of a variety of leaving groups such as alkoxy, hydroxy, halogen, pseudohalogen (including azide, cyanide, isocyanate and isothiocyanate), alkyl or arenesulfonate, aromatic heterocycle(bonded through a heteroatom) and N-hydroxyheterocycle, including hydroxysuccinimide or hydroxybenzotriazole ester. The following definitions apply to the terms above:

| | |
|---|---|
| azide | —N—N≡N |
| cyanide | —C≡N |
| isocyanate | —N=C=O |
| isothiocyanate | —N=C=S |
| alkylsulfonate | —O—S(=O)(=O)-alkyl |
| arenesulfonate | —O—S(=O)(=O)-aryl |

N-hydroxyheterocyclic 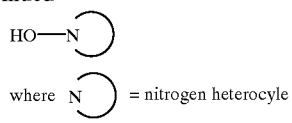

where 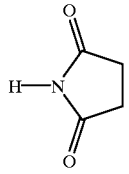 = nitrogen heterocyle

N-hydroxysuccinimide 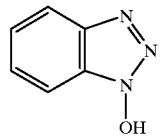

hydrobenzotriazole

The acyl halides (2c, J=halogen) may be prepared using inorganic halogenating agents such as thionyl chloride or bromide, phosphorous trichloride or bromide, phosphorous pentachloride or bromide or organic agents such as oxalyl chloride or trichlorisocyanuric acid. Esters (2c, J=OR") (R" is defined above) may be prepared in a variety of ways starting from the acid chloride 2c where J is Cl by combination with the desired alcohol in the presence of an organic or inorganic base stated previously for the acylation of compound 12a or compound 12b. Alternatively, the ester may be produced by acid-promoted esterification in the presence of the desired alcohol. The sulfonates (2c, J=OSO$_2$W$_1$, where W$_1$ is alkyl or aryl) are typically made by reaction of the carboxylic acid 2b with alkyl or arylsulfonyl chlorides in the presence of an organic amine base such as triethylamine in a non-polar solvent at temperatures below 0° C. Alkyl and arylsulfonyl are defined as follows:

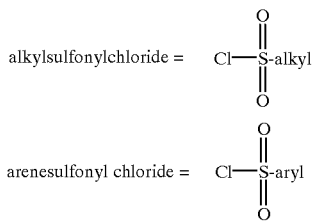

The pseudohalogen derivatives of 2c (J=pseudohalogen) are typically made from the acid halides 2c (J=halogen) by reaction with inorganic pseudohalide in the presence of a base. Such bases include, but are not limited to metal hydroxides, bicarbonates and carbonates or organic bases such as amines like triethylamine, diethylamine, diethyl isopropylamine, 1,8-diazabicyclo[2.2.2]octane (DABCO) or related di- or trialkylamines, as well as amidine bases like 1,8-diazabicyclo[5.4.0]undec-7-ene (DBU) and 1,8-diazabicyclo[4.3.0]non-ene (DBN). A particularly preferred base is triethylamine. The heteroaromatic derivatives of 2c are also made from the acid halides 2c (J=halogen), utilizing the specific heteroaromatic compound in the presence of an amine base in a non-polar solvent. The N-hydroxyheterocyclic derivatives of 2c can be made from the acid halides as above and may also be generated using alkyl carbodiimides (alkyl-N=C=N-alkyl, where the alkyl groups can be the same or different) or aryl carbodiimides (aryl-N=C=N-aryl, where the aryl groups can be the same or different) and an amine base as condensing agents.

The primary or secondary amine (shown above the arrow in Step 2 of Scheme I) used in the coupling process may incorporate suitable protecting groups, depending on the functionality present in the amine and the mode of coupling used. The mode of coupling of 2c with a primary or secondary amine can be carried out in a variety of ways depending on the identity of J. When a free acid is used (2c, J=OH) the coupling can be performed using carbodiimide-based methods utilizing any of the common reagents of this class, including dicyclohexylcarbodiimide or related dialkylcarbodiimides, EDC (salts of 1-(3-dimethylaminopropyl)-3-ethylcarbodiimide) or related water-soluble reagents along with an organic amine base in polar organic solvents such as dioxane, DMF, NMP and acetonitrile in the presence of an N-hydroxyheterocyclic compound such as N-hydroxysuccinimide or 3-hydroxybenzotriazole. Alternatively, haloformate esters, such as 12d, may be used to temporarily activate the acid to give mixed anhydrides of general formula 2d.

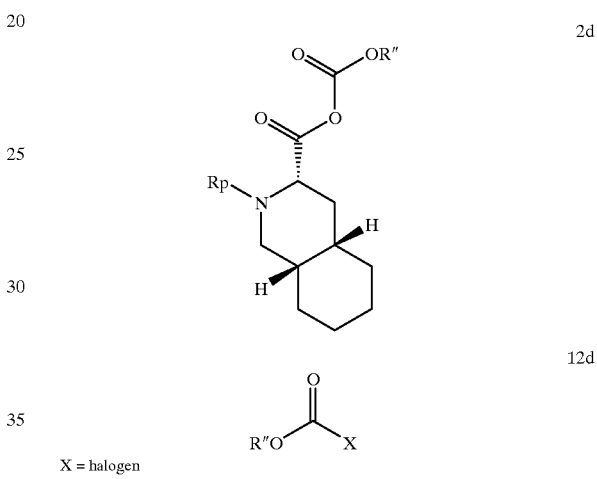

X = halogen

Such haloformate esters are typically as shown in 12d above and include methyl-, ethyl-, isopropyl-, isobutyl-, n-butyl, phenyl- and related alkyl and aryl chloroformates, defined below.

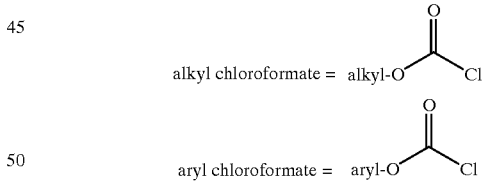

Formula 2d is a possible intermediate in the step from formula 2b to formula 3. Formula 2d is an intermediate, but the process described here results in formula 3, without isolation of Formula 2d.

These reactions are typically performed in a variety of non-polar organic solvents like halocarbons and ethers such as diethyl ether, methyl t-butylether, diisopropyl ether, dioxane and THF at temperatures below 0° C. accompanied by an organic amine base such as triethylamine, diethylamine, diethyl isopropylamine, DABCO or related di- or trialkylamines, as well as amidine bases like DBU and DBN.

When J in compound 2c is an alkyl or arenesulfonate (J=OSO$_2$R or OSO$_2$Ar), the coupling can be performed in a variety of non-polar organic solvents like halocarbons and ethers, such as diethyl ether, methyl t-butylether, diisopropyl ether, dioxane and THF at temperatures below 0° C., accompanied by an organic amine base such as triethylamine, diethylamine, diethyl isopropylamine, DABCO or related di- or trialkylamines, as well as amidine bases like DBU and DBN.

When J in compound 2c is a halogen or pseudohalogen, the coupling may be performed in most common organic solvents such as THF, diethyl ether, dioxane, methyl t-butyl ether or other ethers; acetone, cyclohexanone, methyl isobutylketone and other ketones; esters such as ethyl, methyl and isopropyl acetate; halogenated solvents such as halogenated methanes and ethanes, chlorobenzene and other halogenated benzenes; nitriles such acetonitrile and propionitrile; lower alcohols such as ethanol, isopropanol, t-butanol and related alcohols; and polar organic solvents such as dimethylformamide, dimethylsulfoxide, N-methyl-2-pyrrollidone and related amide-containing solvents. A base is frequently used and may be any of a number of inorganic bases such as metal hydroxides, bicarbonates and carbonates or organic bases such as amines like triethylamine, diethylamine, diethyl isopropylamine, DABCO or related di- or trialkylamines, as well as amidine bases like DBU and DBN.

One skilled in the art will be able to perform the amide coupling Step 2 with other possible J groups.

In Step 3 protecting group removal can be accomplished using any of the standard methods for deprotecting a particular class of protecting group. Simple alkyl- and substituted alkyl carbamates can be removed with aqueous solutions of base at temperatures up to about 100° C., employing any of the common inorganic metal hydroxides such as sodium-, lithium-, potassium- or barium hydroxide or hydroxides of other metals in at least stoichiometric amounts. Carbamate protecting groups that contain benzyl groups bonded to oxygen may be removed by hydrogenolysis with a palladium or platinum catalyst. Alternatively, aqueous base hydrolysis may be used at temperatures up to about 100° C., employing any of the common inorganic metal hydroxides such as sodium-, lithium-, potassium- or barium hydroxide or hydroxides of other metals in at least stoichiometric amounts. A variety of anhydrous acids may also be used for deprotection of benzyl-based carbamates, including HCl, HBr and HI. Lewis acids of boron and aluminum such as $AlCl_3$, $BBr_3$, $BCl_3$ in non-polar solvents are also effective. Certain substituted benzyl, aryl or alkyl groups in which the specific substitution pattern is chosen for its ability to be removed under specific conditions may also be used. For example, the 2-trimethylsilylethylcarbonyl group (Teoc) is a protecting group designed to take advantage of the specific reactivity of the 2-trimethylsilylethyl group in the deprotection process. 2-Trimethylsilylethylcarbonyl chloride may be used to protect the amine nitrogen and may later be removed using sources of fluoride ion such as HF or tetraalkylammonium fluoride salts.

In Step 4, the perhydroisoquinoline piece of formula 4 is connected to the Chloroalcohol (compound 5, Scheme I) via an epoxide intermediate (13) generated via the base-induced closure of the vicinal chlorohydrin functionality.

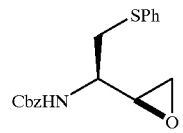

13

Compound 5 is produced by Kaneka Industries, Japan. Several close-open procedures in proceeding from compound 5→compound 13→compound 6 may be used. The epoxide 13 may be isolated or it may be reacted with 4 added either subsequent to formation of 13 or 4 may be present from the beginning of the sequence. The epoxide 13 can be generated using inorganic bases such as metal hydroxides, carbonates and bicarbonates in solvents such as alcohols like methanol ethanol or isopropyl alcohol, ethers such as THF and dioxane or mixtures of the two. The epoxide can also be generated in a 2-phase solvent system consisting of water and a halocarbon solvent such as dichloromethane along with the base. A phase-transfer catalyst such as a tetraalkylammonium salt may be used to facilitate the process. The process of opening the epoxide 13 with compound 4 is accomplished in alcohol solvents or mixtures of an alcohol and another solvent which may be an ether or a dipolar aprotic solvent such as dimethylformamide or dimethylsulfoxide. The opening of the epoxide 13 with compound 4 to give compound 6 is optimally performed over a period of 2–7 hours at 50–60° C.

In Step 5 the carbobenzyloxy group can be removed to give the free amine 7. This can be done using HBr in acetic acid using cosolvents such as halocarbons. It can also be performed using halides of boron such as $BBr_3$ and $BCl_3$ or alkyl substituted boron halides such as dimethylboron bromide in halocarbon solvents like chloroform and dichloromethane at temperatures ranging from 0° C. up to ambient temperature. Alternatively, the carbobenzyloxy group can be removed by hydrolysis using aqueous/alcoholic solutions of metal hydroxides like barium, sodium, lithium or potassium hydroxide at temperatures above ambient for periods of hours.

Step 6a is the coupling of benzoic acid derivatives of formula 8 to give 9a. In Formula 8, Q can be a leaving group. Q can be any of the leaving groups discussed above for Group J. The compounds of formula 8 where Q=OH or Cl are commercially available from EMS Dottikon, Lenzburg, Switzerland and Sugai Chemical Industries, Ltd. in Japan. The coupling can be carried out in a variety of ways, depending on the identity of Q. When a free acid is used (Q=OH), the coupling can be performed using carbodiimide based methods utilizing any of the common reagents of this class including dicyclohexylcarbodiimide or related dialkylcarbodiimides, EDC (salts of 1-(3-dimethylaminopropyl)-3-ethylcarbodiimide) or related water soluble reagents along with an organic amine base in polar organic solvents such as dioxane, DMF, NMP and acetonitrile in the presence of an N-hydroxyheterocyclic including N-hydroxysuccinimide or 3-hydroxybenzotriazole. When Q=a halogen or pseudohalogen, the coupling may be performed in most common organic solvents such as THF, diethyl ether, dioxane, methyl t-butyl ether or other ethers; acetone, cyclohexanone, methyl isobutylketone and other ketones; esters such as ethyl, methyl and isopropyl acetate; halogenated solvents such as halogenated methanes and ethanes, chlorobenzene and other halogenated benzenes; nitriles such acetonitrile and propionitrile; lower alcohols such as ethanol, isopropanol, t-butanol and related alcohols, and polar organic solvents such as dimethylformamide, dimethylsulfoxide, N-methyl-2-pyrrollidone and related amide-containing solvents. A base is frequently used and may be any of a number of inorganic bases such as metal hydroxides, bicarbonates and carbonates or organic bases such as amines like triethylamine, diethylamine, diethyl isopropylamine, DABCO or related di- or trialkylamines, as well as amidine bases like DBU and DBN.

Acetate removal is accomplished in step 6b with aqueous or alcoholic solutions of inorganic bases such as metal hydroxides, carbonates and bicarbonates at ambient temperatures up to 100° C. If there is a protected functionality on the carboxamide group bonded to the perhydroisoquinoline ring system, it is best removed at this point (during or after step 6b). The nature of this step is dependent on the exact identity of the protecting group.

A preferred method for accomplishing the entire process shown in Scheme I is shown in Scheme II.

The Cbz-protected amino acid 15 was coupled with the amine 22 to give the amide 16. The Cbz group was removed by hydrogenation to

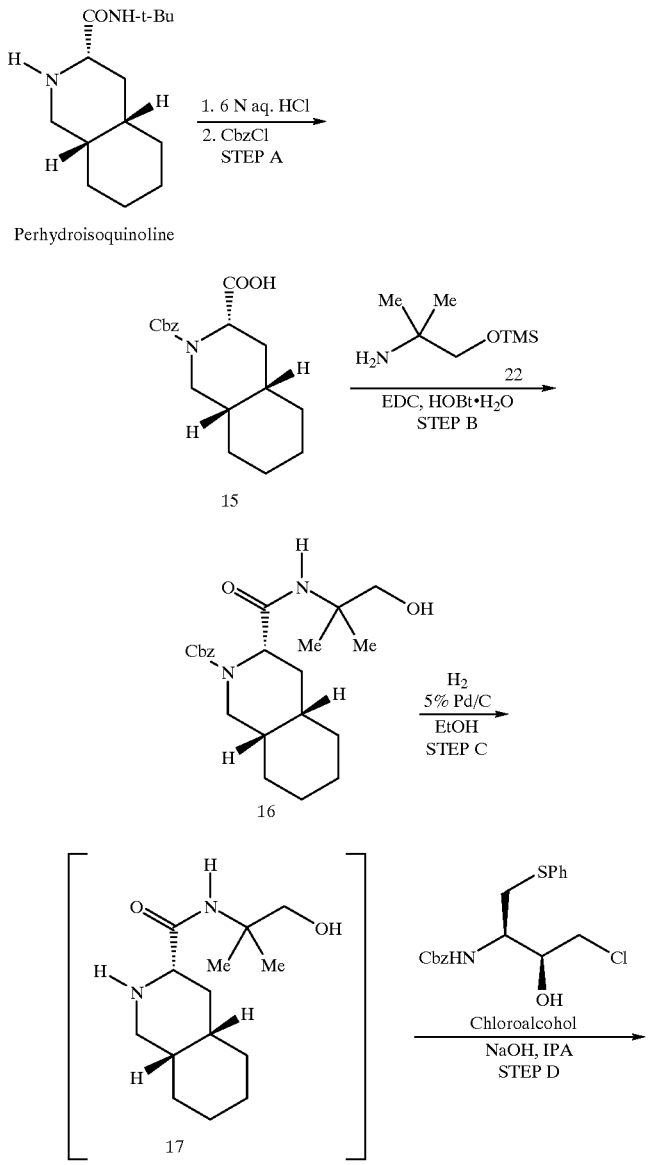

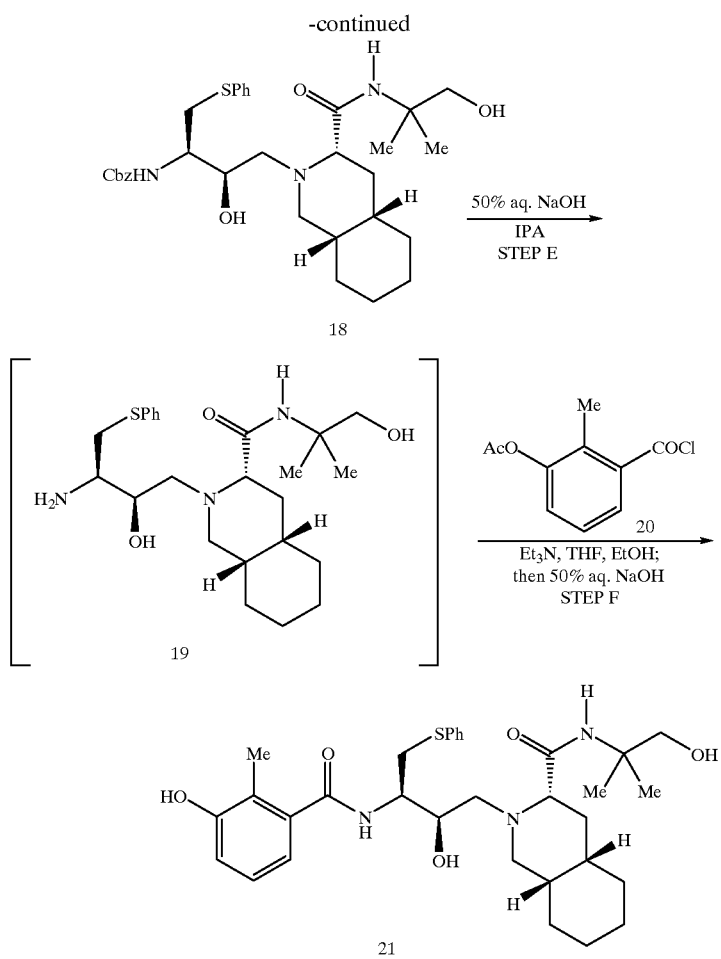

give the amine 17. This was coupled with the chloroalcohol via the epoxide using the in situ procedure to give the adduct 18. Conventional deprotection with base and coupling of the free primary amine with the acid chloride 20 gave rise to amide 21. Details of this process are provided below in Examples 1 A to F. The lettering A to F in Scheme II corresponds to Examples 1 A to F below.

The following Examples illustrate aspects of the invention. These examples are for illustrative purposes and are not intended to limit the scope of the invention.

Abbreviations for the terms melting point, nuclear magnetic resonance spectra, electron impact mass spectra, field desorption mass spectra, fast atom bombardment mass spectra, infrared spectra, ultraviolet spectra, elemental analysis, high performance liquid chromatography, and thin layer chromatography are, respectively, m.p., NMR, EIMS, MS(FD), MS(FAB), IR, UV, Analysis, HPLC, and TLC. In addition, the absorption maxima listed for the IR spectra are those of interest, not all maxima observed.

In conjunction with the NMR spectra, the following abbreviations are used: singlet (s), doublet (d), doublet of doublets (dd), triplet (t), quartet (q), multiplet (m), doublet of multiplets (dm), broad singlet (br.s), broad doublet (br.d), broad triplet (br.t), and broad multiplet (br.m). J indicates the coupling constant in Hertz (Hz). Unless otherwise noted, NMR data refer to the free base of the subject compound.

NMR spectra were obtained on a General Electric QE-300 300 MHz instrument. Chemical shifts are expressed in δ values in ppm. Mass spectra were obtained on a VG ZAB-3 Spectrometer at the Scripps Research Institute, La Jolla, Calif. Infra-red spectra were recorded on a Midac Corporation spectrometer. UV spectra were obtained on a Varian Cary 3E instrument. Thin layer chromatography was carried out using silica plates available from E. Merck. Melting points were measured on a Mettler FP62 instrument and are uncorrected.

EXAMPLE 1

Procedures for the Synthesis of Amide of Formula 21

[3S-[2(2S*,3S*),3 alpha,4a beta,8a beta]]-N-(1,1-dimethyl-2-hydroxyethyl)decahydro-2-[2-hydroxy-3-[(3-hydroxy-2-methylbenzoyl)amino]-4-(phenylthio)butyl]-3-isoquinolinecarboxamide

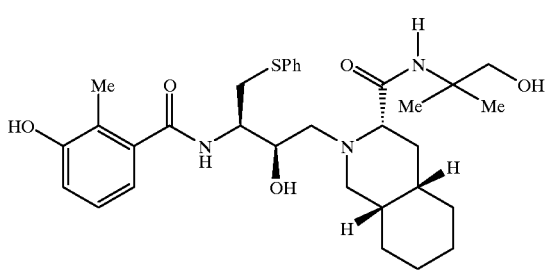

A. Perhydroisoquinoline (26.4 g, 111 mmol) (commerically available from NSC Technologies (Chicago, Ill.) or Procos SpA (Milan, Italy)) was suspended in water (200 mL) and concentrated aqueous HCl (200 mL). This mixture was heated to reflux and stirred for 3 days, during which time it went into solution. The solvents were removed under reduced pressure to give a light yellow solid. The solid was slurried in 2-propanol (200 mL) and filtered. The filtrate was evaporated under reduced pressure to an oil. EtOAc (100 mL) and water (100 mL) were added and the pH of the solution was brought to 8.0 by the addition of 2 N aqueous KOH. Benzyl chloroformate (15.8 mL, 111 mmol) was added dropwise over 30 minutes and the pH was kept between 7 and 8 by the addition of 2 N aqueous KOH. The mixture was stirred at room temperature for 18 hours. EtOAc (200 mL) was added and the organic layer was washed with 1 N aqueous HCl (100 mL), and brine (100 mL). The organic layer was dried (MgSO$_4$), filtered, and evaporated under reduced pressure to an oil. The product was purified by silica gel chromatography, eluting with 1:1 40–60 petroleum ether/EtOAc followed by 100% EtOAc. The fractions containing product were collected and evaporated under reduced pressure to give the compound 15 (11.3 g, 32%) as a colorless oil: $^1$H NMR (300 MHz, CDCl$_3$) δ 7.43–7.28 (m, 5 H), 5.17 (br s, 2 H), 4.76 (m, 1 H), 3.79 (m, 1 H), 3.33 (m, 1 H), 2.19 (m, 1 H), 1.96 (m, 1 H), 1.88–1.15 (m, 10 H)

B. 1-Hydroxybenzotriazole (4.2 g, 31.4 mmol) and EDC (6.0 g, 31.4 mmol) were added to a solution of acid 15 (8.3 g, 26.2 mmol) in DMF (128 mL) at ambient temperature. The mixture was heated at 80° C. for 10 minutes. 1,1-Dimethyl-2-trimethylsilyloxyethylamine (5.1 g, 31.4 mmol, prepared from 1,1-dimethyl-2-hydroxyethylamine (Aldrich Chemical Co.) and hexamethyldisilazane (Aldrich Chemical Co.)) by heating the mixture neat under reflux for several hours followed by evaporation of the volatile components was added and the solution was heated at 80° C. for 17 hours. The yellow solution was poured into EtOAc (250 mL) and 2 N aqueous HCl (250 mL). After stirring for 10 minutes EtOAc (750 mL) was added and the mixture was washed with H$_2$O (3×500 mL) and brine (1×250 mL). The combined aqueous layers were extracted with EtOAc (1×250 mL). The combined organic layers were dried (Na$_2$SO$_4$) and purified by flash chromatography (50/50 EtOAc/hexanes) to give the compound 16 as a colorless oil (7.9 g, 78%): $^1$H NMR (300 MHz, CD$_3$OD) δ 7.36 (m, 5 H), 5.20 (d, J=8.1 Hz, 1 H), 5.10 (m, 1 H), 4.53 (m, 1 H), 3.78 (dd, J=13.2, 4.4 Hz, 1 H), 3.60 (m, 2 H), 3.48 (d, J=10.7 Hz, 1 H), 2.15–1.25 (m, 12 H), 1.31 (s, 3 H), 1.29 (s, 3 H).

C. A mixture of carbamate 16 (7.9 g, 20.4 mmol) and 5% palladium on carbon (Pd/C) (1.6 g) was hydrogenated at 50 psi H$_2$ in absolute EtOH (110 mL) at ambient temperature for 18 hours. The mixture was filtered through Celite and evaporated in vacuo to give amine 17 as a white, crystalline solid: $^1$H NMR (300 MHz, CD$_3$OD) δ 3.63 (q, J=7.0 Hz, 2 H), 3.34 (m, 1 H), 3.27 (dd, J=11.8, 3.3 Hz, 1 H), 2.91 (m, 1 H), 2.02–1.15 (m, 12 H), 1.32 (s, 3 H), 1.31 (s, 3 H).

D. Aqueous 10.2 N NaOH (2.4 mL, 24.5 mmol) was added to a warm (27° C.) suspension of chloroalcohol (obtained from Kaneka Industries in Japan) (10.4 g, 28.6 mmol) in isopropanol (IPA)(104 mL) with mechanical stirring. After 1 hour 1 N aqueous HCl in IPA (prepared by addition of 1 mL of concentrated aqueous HCl to 12 mL of IPA) approximately (ca.) 1 mL) was added to neutralize (pH=7). Amine 17 (5.2 g, 20.4 mmol) was added as a solution in IPA (50 mL) and the thin suspension was heated at 60° C. for 10 hours. The IPA was removed in vacuo. The residue was diluted with EtOAc (150 mL) and washed with H$_2$O (2×50 mL), saturated aqueous NaHCO$_3$ (1×50 mL), and brine (1×50 mL). The combined aqueous layers were extracted with EtOAc (1×25 mL). The combined organic layers were dried (Na$_2$SO$_4$) and purified by flash chromatography (75/25 EtOAc/hexanes, then EtOAc) to give the compound 18 as a white solid (8.98 g, 76%) : $^1$H NMR (300 MHz, CD$_3$OD) δ 7.33 (m, 10 H) , 5.08 (AB, JAB =12.2 Hz, Δu$_{AB}$=12.1 Hz, 2 H) , 3.96, (m, 2 H) , 3.56 (q, J=7.3 Hz, 2 H), 3.50, (m, 1 H), 3.20 (dd, J=13.6, 9.2 Hz, 1 H), 3.03 (m, 1 H), 2.64 (m, 2 H), 2.20–1.20 (m, 14 H), 1.28 (s, 6 H).

E. 50% aqueous NaOH (2.7 g, 1.8 mL, 33.6 mmol) was added to a suspension of carbamate 18 (6.75 g, 11.6 mmol) in IPA (34 mL) at ambient temperature. The mixture was heated under reflux for 12 hours. After cooling to ambient temperature, the mixture was diluted with methyl t-butyl ether (MTBE) (600 mL) and washed with H$_2$O (2×250 mL) and brine (1×125 mL). The combined aqueous layers were extracted with MTBE (1×150 mL). The combined organic layers were dried (Na$_2$SO$_4$) and evaporated in vacuo to give a mixture of compound 19 and benzyl alcohol as an oily white solid: $^1$H NMR (300 MHz, CD$_3$OD) δ 7.34 (m, 10 H) , 4.63 (s, 2 H) , 3.81 (m, 1 H), 3.58 (m, 3 H), 3.03–2.60 (m, 5 H), 2.17 (m, 1 H), 2.05 (m, 1 H), 1.87–1.05 (m, 12 H), 1.30 (s, 3 H), 1.28 (s, 3 H).

F. Triethylamine (3.2 g, 4.3 mL, 31.2 mmol) was added to a solution of the mixture of amine 19 (4.7 g, 10.4 mmol theory from 18) and benzyl alcohol in EtOH (23 mL) at ambient temperature. A solution of 3-acetoxy-2-methylbenzoyl chloride (20)(obtained according to procedures set forth in U.S. patent application Ser. No. 08/708,411, filed Sep. 5, 1996, which is specifically incorporated by reference herein) (2.4 g, 11.5 mmol) in THF (4 mL) was added. After 2 hours 50% aqueous NaOH (4.1 g, 2.8 mL, 52.2 mmol) was added and the mixture was heated under reflux for 1 hour. After cooling to ambient temperature, the mixture was neutralized to pH=7 with 2 N aqueous HCl (26 mL). This mixture was diluted with EtOAc (500 mL) and washed with H$_2$O (1×250 mL), saturated aqueous NaHCO$_3$ (2×250 mL), H$_2$O (1×250 mL), and brine (1×125 mL). The organic layer was dried (Na$_2$SO$_4$) and purified by flash chromatography (75/25 EtOAc/hexanes) to give amide 21 as a white foam (1173-57A, 1.39 g, 23%). The $^1$H NMR indicated the presence of 11 wt % EtOAc which could not be removed in vacuo.

Analysis: $^1$H NMR (300 MHz, CD$_3$OD) δ 7.53 (d, J=7.3 Hz, 2 H), 7.32 (t, J=7.0 Hz, 2 H), 7.20 (t, J=7.3 Hz, 1 H), 7.06 (t, J=8.1 Hz, 1 H), 6.92 (d, J=8.1 Hz, 1 H), 6.83 (d, J=8.1 Hz, 1 H), 4.42 (m, 1 H), 4.08 (m, 1 H), 3.61 (dd, J=13.6, 4.0 Hz, 1 H), 3.45 (AB, J$_{AB}$=11.0 Hz, Δu$_{AB}$=18.0 Hz, 2 H), 3.29 (dd, J=13.6, 10.3 Hz, 1 H), 3.10 (m, 1 H), 2.66 (m, 2 H), 2.28 (s, 3 H), 2.22 (m, 2 H), 2.04 (m, 1 H), 1.86–1.20 (m, 11 H), 1.19 (s, 3 H), 1.18 (s, 3 H).

$^{13}$C NMR (75.5 MHz, CD$_3$OD) δ 175.7, 172.5, 155.9, 138.8, 136.7, 129.8, 128.9, 126.3, 126.0, 122.4, 118.4, 115.9, 70.3, 69.9, 68.2, 59.3, 58.8, 54.9, 53.0, 36.5, 34.2, 34.1, 31.1, 30.7, 26.4, 26.0, 23.1, 23.0, 20.8, 12.1.

EXAMPLE 2

HIV Protease inhibition activity and anti HIV activity in cell culture of compound 21

Tight binding kinetics analysis was used to determine the magnitude of the K$_i$ values of compound 21. The K$_i$=5.6±0.91 nM.

Methods

Expression of HIV-1 protease

HIV-1 protease gene was isolated from the viral strain IIIB (Ratner, L. et al., Nature, 316, 227–284 (1985)). In order to increase the stability of purified protease (Rose, J. R. et al., J. Biol. Chem., 268, 11939–11945 (1993)), the glutamine residue at position 7 (Q7) was mutated to serine (S) by replacing the 33 base pairs segment between the NdeI and BstEII sites of the protease gene sequence with synthetic oligonucleotides encoding the Q7S mutation. The modified gene sequence was inserted into the plasmid vector pGZ (Menge, K. L. et la., Biochemistry, 34:15934–15942 (1995) under the control of phage T7 promoter. The resulting construct, pGZ/HP-19Q7S#9, was transformed into *E. coli* strain BL21(DE3) purchased from Novagen, Inc.

Expression of HIV-1 PR: Cultures were grown in 2YT media (1.6% Trypticase Pepton, 1% Yeast extract, 0.5% NaCl at an initial pH 7.5) containing 200 μg/L ampicillin in 100 L fermentor (Biolafitte SA) at 37° C. for 5 hours and then induced by addition of 1 mM IPTG (Isopropyl-β-D-thiogalactopyranoside). The temperature of the culture during induction was raised to 42° C. to increase accumulations of the recombinant HIV-1 protease as insoluble inclusion bodies. After 2 hours at 42° C., cells were harvested by crossflow filtration using Pellicon 0.1 μm VVPPOOOC$_5$ cassette #10 (Millipore) and the cell paste was stored frozen at −70° C.

Purification of Recombinant HIV-1 Protease: All steps unless otherwise indicated were carried out at 4° C. Protein concentrations were determined using BioRad protein assay solution with bovine serum albumin (BioRad, Richmond, Calif.) as a standard. Chromatographic steps and the purity of HIV PR was analyzed by sodium dodecylsulfate polyacrylamide gel electrophoresis (SDS-PAGE). Final purity of HIV-PR was>98%. Typical final yield from each 100 L culture was ~120 mg.

Cell paste from 100L culture was resuspended in 300 mL of lysis buffer (50 mM Tris-Cl pH 8.0, 25 mM NaCl, 20 mM 2-mercaptoethanol) and microfluidized in Microfluidics Corporation fluidizer at 22,000 psi. The crude cell lysate was clarified by centrifugation at 14,000 rpm for 20 minutes. HIV PR was found predominantly in the pellet in the form of inclusion bodies. The inclusion bodies were subsequently washed multiple times in the lysis buffer containing in addition 0.1% Trition-X100 and 1 M urea, and after each washing procedure, the inclusion bodies were pelleted by centrifugation at 5,000 rpm for 20 minutes. Purified inclusion bodies were solubilized in buffer containing 50 mM Tris-Cl, pH 8.0, 25 mM NaCl, 20 mM 2-mercaptoethanol, and 8 M urea. Solution was clarified by centrifugation at 14,000 rpm and applied at room temperature to a 300 mL Fast Flow Q-Sepharose column (Pharmacia, Piscataway, N.J.) equilibrated with the same buffer. Under these conditions HIV PR did not bind to the column and essentially pure enzyme was found in the flow-through fractions. To renature the protein, the fractions from Fast Flow Q-Sepharose column were dialyzed against three changes of buffer containing 25 mM NaH2PO4 pH 7.0, 25 mM NaCl, 10 mM DTT and 10% glycerol. After refolding, small quantities of precipitated material were removed by centrifugation and resultant enzyme preparation were concentrated, dialyzed against 0.5 M NaCl, 50 mM MES pH 5.6, 10 mM DTT, frozen in small aliquots at ~2 mg/mL and stored at −70°.

Tight-Binding Kinetics Assay and Analysis

Proteolytic activity of purified HIV-1 protease was measured using a modified chromogenic assay developed by Richards at al. (Richards, A. D. et al. J. Biol. Chem., 256, 773–7736 (1990)). The synthetic peptide His-Lys-Ala-Arg-Val-Leu-Phe(paraNO2)-Glu-Ala-Nle-Ser-NH$_2$ (American Peptide Company) (Nle is norleucine) was used as a substrate. The assay was carried out in 0.5 M NaCl, 50 mM MES pH 5.6, 5 mM DDT, and 2% DMSO at 37° C. Cleavage of the scissile bond between leucine and paranitrophenylalanine (Phe para-NO2) was assayed by spectrophotometric monitoring of the decrease on absorbance at 305 nm. Initial velocity was determined as the rate of decline of absorbance during the first 100 seconds of the enzymatic reaction. Under these conditions, and using Q7S HIV-1 protease, the Michaelis constant (Km) for this substrate is 59±17 μM.

For determination of the inhibition of compound 21, a saturating concentration of substrate of 200 uM was used. Between 13 and 20 concentrations of inhibitors were evaluated and the velocity of reaction was measured at each concentration as described above. The apparent Ki (Ki app), set forth above, was determined by computer assisted non-linear least square fitting of the data to the tight binding equation of Morrison (Morrison, J. F., Biochem. Biophys. Acta, 185, 269–286 (1963)).

EXAMPLE 3

Antiviral activity of compound 21 against HIV-1 in cell culture

Cells and virus strains

The CEM-SS and MT-2 human T cell lines and HIV-1 strains RF and IIIB were obtained from the AIDS Research and Reference Program, Division of AIDS, NIAID, and NIH.

Cell protection assays

The inhibitory effects of each agent on HIV-1 replication were measured by the MTT dye reduction method (Alley, M. C. et al., Cancer Res. 48: 589–601 (1988)). Compounds were dissolved in DMSO at a concentration of 40 mg/ml then diluted 1:200 in culture medium (RPMI, supplemented with 10% fetal bovine serum). From each diluted stock, 100 μl was added to a 96-well plate and serial half-log dilutions were prepared. In separate tubes, MT-2 cells and CEM-SS cells were infected with HIV-1 IIIB or HIV-1 RF at a multiplicity of infection (m.o.i.) of 0.01 and 0.03, respectively. Following a 4-hour adsorption period, loo Al of infected or uninfected cells were added to the wells of the drug containing plate to give a final concentration of 1×10$^4$ cells/well. Six days (CEM-SS cells) or 7 days (MT-2 cells) later, MTT (5 mg/ml) was added to test plates and the amount of formazan produced was quantified spectrophotometrically at 570 nm. Data were expressed as the percentage of formazan produced in drug-treated cells compared to formazan produced in wells of uninfected, drug-free cells. The EDS$_{50}$ was calculated as the concentration of drug that increased the percentage of formazan production in infected, drug-treated cells to 50% of that produced by uninfected, drug-free cells. Cytotoxicity ($TC_{50}$) was calculated as the concentration of drug that decreased the percentage of formazan produced in uninfected, drug-treated cells to 50% of that produced in uninfected, drug-free cells. The therapeutic index (TI) was calculated by dividing the cytotoxicity ($TC_{50}$) by the antiviral efficacy ($ED_{50}$).

TABLE 1

Antiviral Activity and Cytotoxicity Evaluations of Compound 21 in an Acute Infection of CEM-SS cells with HIV-1 RF

| Compound | $ED_{50}$ (nM) | $ED_{95}$ (nM) | $TC_{50}$ (µM) | Therapeutic index [a] |
|---|---|---|---|---|
| 21 | 34.2 | 154.1 | 96.6 | 2825 |
| azidophymidine (AZT) | 52.3 | 543.1 | >374.5 | >7161 |
| dideoxycytidine (ddC) | 94.70 | 142.0 | 37.69 | 398 |

[a] Therapeutic index = Cytotoxicity ($TC_{50}$) ÷ Antiviral activity ($ED_{50}$).

TABLE 2

Antiviral Activity and Cytotoxicity Evaluations of Compound 21 in an Acute Infection of MT-2 cells with HIV-1 IIIB

| Compound | $ED_{50}$ (nM) | $ED_{95}$ (nM) | $TC_{50}$ (µM) | Therapeutic |
|---|---|---|---|---|
| 21 | 85.6 | ND | 92.6 | 1082 |
| AZT | 430.7 | ND | 109.4 | 254 |
| ddC | 5924 | ND | 176.3 | 30 |

[a] Therapeutic index = Cytotoxicity ($TC_{50}$) ÷ Antiviral activity ($ED_{50}$).

As noted above, the compounds of the present invention are useful for inhibiting HIV protease, which is an enzyme associated with viral component production and assembly. An embodiment of the present invention is a method of treating HIV infection comprising administering to a host or patient, such as a primate, an effective amount of a compound of formula (9) or a pharmaceutically acceptable salt thereof. Another embodiment of the present invention is a method of treating AIDS comprising administering to a host or patient an effective amount of a compound of formula (9) or a pharmaceutically acceptable salt thereof. A further embodiment of the present invention is a method of inhibiting HIV protease comprising administering to an HIV infected cell or a host or patient, such as a primate, infected with HIV, an effective amount of a compound of formula (1) or a pharmaceutically acceptable salt thereof.

The term "effective amount" means an amount of a compound of formula (9) or its pharmaceutically acceptable salt that is effective to inhibit the HIV protease mediated viral component production and assembly. The specific dose of compound administered according to this invention to obtain therapeutic or inhibitory effects will, of course, be determined by the particular circumstances surrounding the case, including, for example, the compound administered, the route of administration, the condition being treated and the individual host or patient being treated. An exemplary daily dose (administered in single or divided doses) contains a dosage level of from about 0.01 mg/kg to about 50 mg/kg of body weight of a compound of this invention. Preferred daily doses generally are from about 0.05 mg/kg to about 40 mg/kg and, more preferably, from about 1.0 mg/kg to about 30 mg/kg.

The compounds of the invention may be administered by a variety of routes, including oral, rectal, transdermal, subcutaneous, intravenous, intramuscular and intranasal routes. The compounds of the present invention are preferably formulated prior to administration. Therefore, another embodiment of the present invention is a pharmaceutical composition or formulation comprising an effective amount of a compound of formula (9) or a pharmaceutically acceptable salt thereof and a pharmaceutically acceptable carrier, such as a diluent or excipient therefor.

The active ingredient preferably comprises from 0.1% to 99.9% by weight of the formulation. By "pharmaceutically acceptable" it is meant that the carrier, such as the diluent or excipient, is compatible with the other ingredients of the formulation and not deleterious to the host or patient.

Pharmaceutical formulations may be prepared from the compounds of the invention by known procedures using known and readily available ingredients. In making the compositions of the present invention, the active ingredient will usually be admixed with a carrier, or diluted by a carrier, or enclosed within a carrier, which may be in the form of a capsule, sachet, paper or other suitable container. When the carrier serves as a diluent, it may be a solid, semi-solid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments (containing, for example, up to 10% by weight of the active compound), soft and hard gelatin capsules, suppositories, sterile injectable solutions, sterile packaged powders and the like.

The following formulation examples are illustrative only and are not intended to limit the scope of the invention. The term "active ingredient" represents a compound of formula (9) or a pharmaceutically acceptable salt thereof.

Formulation 1

Hard gelatin capsules are prepared using the following ingredients:

| | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

| | Quantity (mg/tablet) |
|---|---|
| Active ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

Formulation 3

An aerosol solution is prepared containing the following components:

|  | Weight |
| --- | --- |
| Active ingredient | 0.25 |
| Methanol | 25.75 |
| Propellant 22 | 74.00 |
| (Chlorodifluoromethane) | |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

|  | Quantity (mg/tablet) |
| --- | --- |
| Active ingredient | 60 |
| Starch | 45 |
| Microcrystalline cellulose | 35 |
| Polyvinylpyrrolidone (as 10% solution in water) | 4 |
| Sodium carboxymethyl starch | 4.5 |
| Magnesium stearate | 0.5 |
| Talc | 1 |
| Total | 150 |

The active ingredient, starch and cellulose are passed through a No. 45 mesh U.S. sieve and mixed thoroughly. The aqueous solution containing polyvinylpyrrolidone is mixed with the resultant powder, and the mixture then is passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules, each containing 80 mg of active ingredient, are made as follows:

|  | Quantity (mg/capsule) |
| --- | --- |
| Active ingredient | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories, each containing 225 mg of active ingredient, are made as follows:

| Active ingredient | 225 mg |
| --- | --- |
| Saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| Active ingredient | 50 mg |
| --- | --- |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethylcellulose and syrup to form a smooth paste. The benzoic acid solution, flavor and color are diluted with a portion of the water and added, with stirring. Sufficient water is then added to produce the required volume.

Formulation 8

An intravenous formulation is prepared as follows:

| Active ingredient | 100 mg |
| --- | --- |
| Isotonic saline | 1,000 mL |

The solution of the above ingredients generally is administered intravenously to a subject at a rate of 1 ml per minute.

Formulation 9

A tablet is prepared using the ingredients below:

|  | Quantity (mg/tablet) |
| --- | --- |
| Active ingredient | 292 mg |
| calcium silicate | 146 mg |
| crospovidone | 146 mg |
| Magnesium stearate | 5 mg |
| Total | 589 mg |

We claim:

1. A compound of the formula:

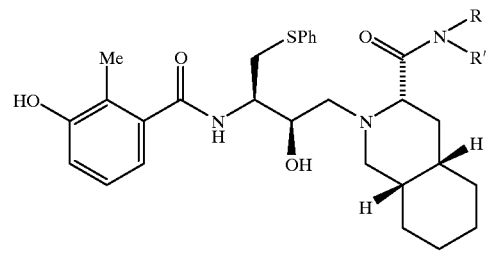

wherein

R and R' are independently selected from H, a substituted or unsubstituted alkyl-$OR_1$ group, a cycloalkyl group substituted with a (C₁–C₆)alkyl group or a (C₁–C₆) alkyl-OH group, a heterocycle group substituted with a (C₁–C₆) alkyl group or a (C₁–C₆)alkyl-OH group, an alkyl-NR₂R₃ group, or an alkyl-S(X)(Y)R₁ group, wherein R₁ is H, a substituted or unsubstituted alkyl group, or an acyl group;

R₂ and R₃ are each independently selected from H, substituted or unsubstituted alkyl, cycloalkyl, heterocyle, and aryl groups, and acyl and sulfonyl groups;

R₁ is H, a substituted or unsubstituted alkyl, cycloalkyl, heterocycle, or aryl group; and X and Y are each independently selected from =O and nothing;

so long as at least one of R and R' is a cycloalkyl group substituted with a (C₁–C₆)alkyl group or a (C₁–C₆)alkyl-OH group, and said cycloalkyl group is selected from:

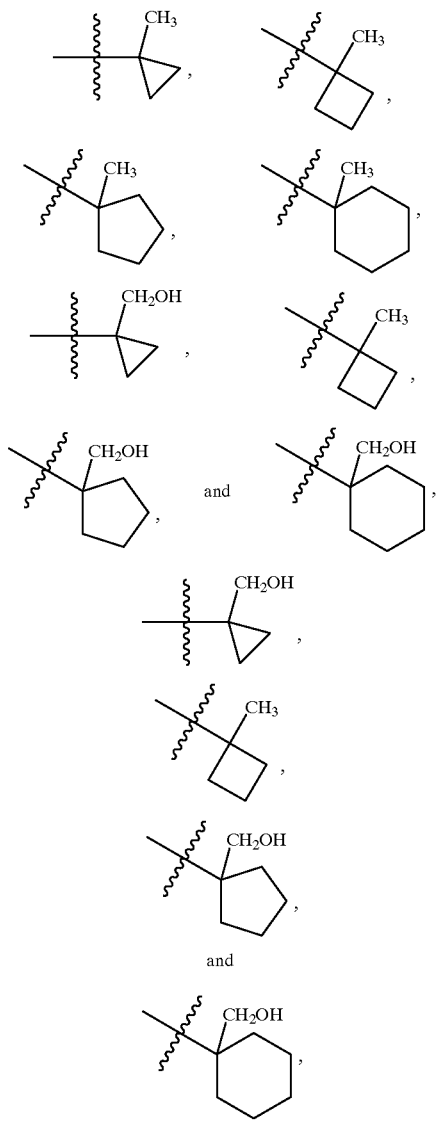

or a pharmaceutically acceptable prodrug, salt or solvate thereof.

2. A compound according to claim 1, wherein R is H, or a pharmaceutically acceptable prodrug, salt, or solvate thereof.

3. A compound of the formula:

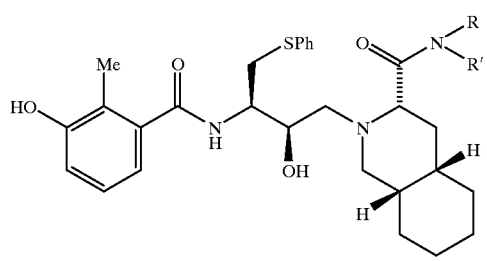

wherein

R and R' are independently selected from H, a substituted or unsubstituted alkyl-OR₁ group, a cycloalkyl group substituted with a (C₁–C₆)alkyl group or a (C₁–C₆) alkyl-OH group, a heterocycle group substituted with a (C₁–C₆alkyl group or a (C₁–C₆)alkyl-OH group, an alkyl-NR₂R₃ group, or an alkyl-S(X)(Y)R₄ group, wherein R₁ is H, a substituted or unsubstituted alkyl group, or an acyl group;

R₂ and R₃ are each independently selected from H, substituted or unsubstituted alkyl, cycloalkyl, heterocycle, and aryl groups, and acyl and sulfonyl groups;

R₄ is H, a substituted or unsubstituted alkyl, cycloalkyl, heterocycle, or aryl group; and X and Y are each independently selected from =O and nothing;

so long as at least one of R and R' is a heterocycle group substituted with a (C₁–C₆)alkyl group or a (C₁–C₆)alkyl-OH group, and said heterocycle group is selected from:

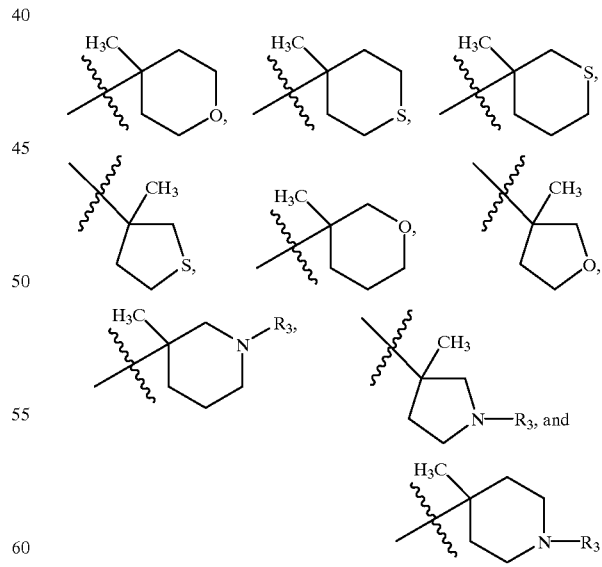

wherein R₃ is H, a substituted or unsubstituted alkyl, cycloalkyl, heterocycle, or aryl group, or an acyl or sulfonyl group, or a pharmaceutically acceptable prodrug, salt or solvate thereof.

4. A compound of the formula:

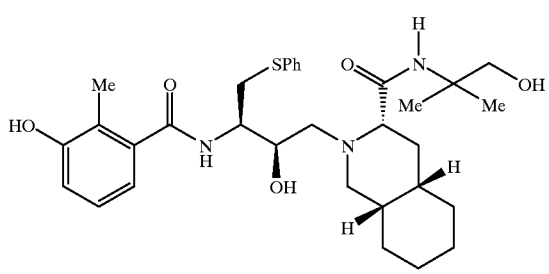

or a pharmaceutically acceptable prodrug, salt or solvate thereof.

5. A compound of the formula:

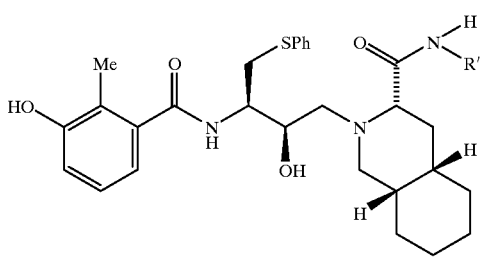

wherein R' is a cycloalkyl group substituted with a $(C_1-C_6)$alkyl group or a $(C_1-C_6)$alkyl-OH group, and said cycloalkyl group is selected from:

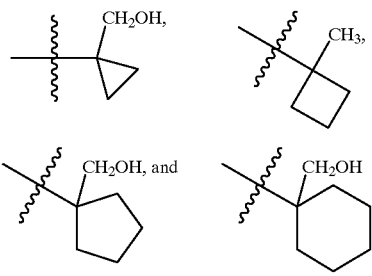

or a pharmaceutically acceptable prodrug, salt or solvate thereof.

6. A salt according to claim 1, having the formula

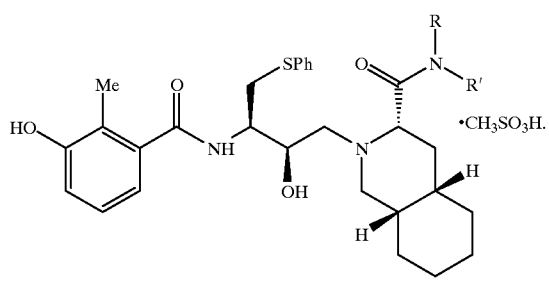

7. A pharmaceutical composition comprising:
(a) an effective amount of compound of claim 1; and
(b) a pharmaceutically acceptable carrier therefor.

8. A pharmaceutical composition comprising:
(a) an effective amount of compound of claim 4; and
(b) a pharmaceutically acceptable carrier therefor.

9. A method of inhibiting HIV protease, comprising administering to a host an effective amount of compound of claim 1 or a pharmaceutically acceptable prodrug, salt or solvate thereof.

10. A method of inhibiting HIV protease, comprising administering to a host an effective amount of a compound of claim 4 or a pharmaceutically acceptable prodrug, salt, or solvate thereof.

11. A compound according to claim 1, which has a purity of more than 90%.

12. A compound according to claim 1, which has a purity of at least 95%.

13. A compound according to claim 1, which has a purity of at least 97%.

14. A compound according to claim 1, which has a purity of at least 99%.

15. A compound according to claim 4, which has a purity of more than 90%.

16. A compound according to claim 4, which has a purity of at least 95%.

17. A compound according to claim 4, which has a purity of at least 97%.

18. A compound according to claim 4, which has a purity of at least 99%.

19. A pharmaceutical composition according to claim 7, wherein the compound has a purity of more than 90%.

20. A pharmaceutical composition according to claim 7, wherein the compound has a purity of at least 95%.

21. A pharmaceutical composition according to claim 7, wherein the compound has a purity of at least 97%.

22. A pharmaceutical composition according to claim 7, wherein the compound has a purity of at least 99%.

23. A pharmaceutical composition according to claim 8, wherein the compound has a purity of more than 90%.

24. A pharmaceutical composition according to claim 8, wherein the compound has a purity of at least 95%.

25. A pharmaceutical composition according to claim 8, wherein the compound has a purity of at least 97%.

26. A pharmaceutical composition according to claim 8, wherein the compound has a purity of at least 99%.

27. A method according to claim 9, wherein the compound has a purity of more than 90%.

28. A method according to claim 9, wherein the compound has a purity of at least 95%.

29. A method according to claim 9, wherein the compound has a purity of at least 97%.

30. A method according to claim 9, wherein the compound has a purity of at least 99%.

31. A method according to claim 10, wherein the compound has a purity of more than 90%.

32. A method according to claim 10, wherein the compound has a purity of at least 95%.

33. A method according to claim 10, wherein the compound has a purity of at least 97%.

34. A method according to claim 10, wherein the compound has a purity of at least 99%.

* * * * *

UNITED STATES PATENT AND TRADEMARK OFFICE
CERTIFICATE OF CORRECTION

PATENT NO. : 6,001,851
DATED : December 14, 1999
INVENTOR(S) : Kim F. Albizati et al.

It is certified that error appears in the above-identified patent and that said Letters Patent is hereby corrected as shown below:

Title page,
Item [75], Inventors, "Siegfried H. Reichi" should read -- Siegfried H. Reich -- and "Takuo Kobayashi, Takasuki" should read -- Takuo Kobayashi, Osaka --.

References Cited,
Item [56], OTHER PUBLICATIONS, after "Tim F. Tam et al.", "Potent" should read -- Potent Inhibition --.

Item [56], Attorney, Agent or Firm, after "Primary Examiner - Zinna Northington Davis" please insert -- Agent, Attorney, or Firm - Fitzpatrick, Cella, Harper & Scinto --.

Column 3,
Lines 40-45, " 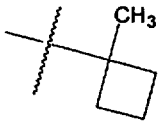 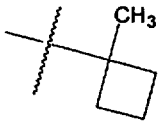 " should be deleted; and

Lines 51-67, " 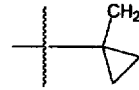 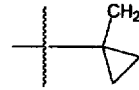

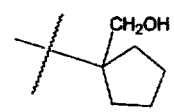

and

" should be deleted.

Column 4,
Lines 1-8, " - continued " should be deleted

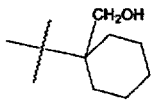

UNITED STATES PATENT AND TRADEMARK OFFICE
CERTIFICATE OF CORRECTION

PATENT NO. : 6,001,851
DATED : December 14, 1999
INVENTOR(S) : Kim F. Albizati et al.

It is certified that error appears in the above-identified patent and that said Letters Patent is hereby corrected as shown below:

Column 13,
Lines 26-37, " 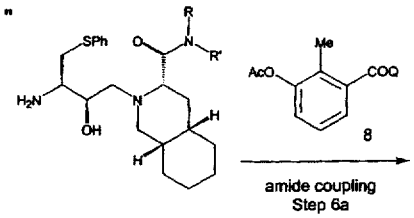 " should be deleted.

Column 17,
Line 57, "diazabicyclo[4.3.0]non-ene" should read -- diazabicyclo[4.3.0]non-5-ene --.

Column 19,
Line 64, "Chloroalcohol" should read -- chloroalcohol --.

Column 26,
Line 22, "JAB" should read -- $J_{AB}$ --;
Line 38, "SH" should read -- 5H --.

Column 28,
Line 13, "773-7736" should read -- 7733-7736 --;
Line 17, "DDT," should read -- DTT, --; and
Line 56, "loo Al" should read -- 100 µl --.

Column 29,
Table 2, "TC50 (µM)   Therapeutic" should read -- TC50 (µM)   Therapeutic Index --

UNITED STATES PATENT AND TRADEMARK OFFICE
CERTIFICATE OF CORRECTION

PATENT NO. : 6,001,851
DATED : December 14, 1999
INVENTOR(S) : Kim F. Albizati et al.

It is certified that error appears in the above-identified patent and that said Letters Patent is hereby corrected as shown below:

Column 33,
Lines 30-35, " 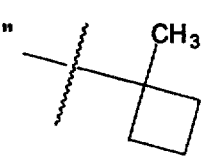 " should be deleted; and

Lines 40-62, 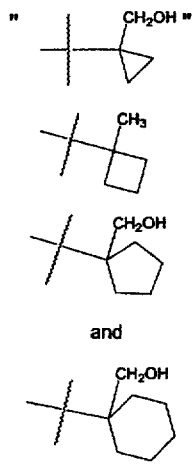 should be deleted.

Signed and Sealed this

Eleventh Day of December, 2001

Attest:

NICHOLAS P. GODICI
Attesting Officer   Acting Director of the United States Patent and Trademark Office

UNITED STATES PATENT AND TRADEMARK OFFICE
CERTIFICATE OF CORRECTION

PATENT NO. : 6,001,851
DATED : December 14, 1999
INVENTOR(S) : Kim F. Albizati et al.

It is certified that error appears in the above-identified patent and that said Letters Patent is hereby corrected as shown below:

Column 33,
Line 44, "alkyl-S(X)(Y)$R_1$" should read -- alkyl-S(X)(Y)$R_4$ --; and
Line 12, "$R_1$" should read -- $R_4$ --.

Signed and Sealed this

Twenty-second Day of October, 2002

*Attest:*

JAMES E. ROGAN
*Attesting Officer*     *Director of the United States Patent and Trademark Office*